United States Patent [19]

Lee

[11] Patent Number: 4,529,882
[45] Date of Patent: Jul. 16, 1985

[54] COMPTON SCATTERING GAMMA RADIATION CAMERA AND METHOD OF CREATING RADIOLOGICAL IMAGES

[75] Inventor: Denny L. Y. Lee, Andover, Mass.

[73] Assignee: E. I. du Pont de Nemours & Company, Wilmington, Del.

[21] Appl. No.: 406,322

[22] Filed: Aug. 9, 1982

[51] Int. Cl.$^3$ .............................................. G01T 1/24
[52] U.S. Cl. ................................. 250/363 S; 250/370
[58] Field of Search ........... 250/370 G, 370 E, 363 S; 378/6, 7

[56] References Cited

U.S. PATENT DOCUMENTS

| | | | |
|---|---|---|---|
| 3,699,340 | 10/1972 | Hick et al. ........................ | 250/370 E |
| 4,047,037 | 9/1977 | Schlosser et al. .................... | 250/370 |
| 4,055,765 | 10/1977 | Gerber et al. ........................ | 250/370 |
| 4,258,428 | 3/1981 | Woronowicz ........................ | 364/527 |

OTHER PUBLICATIONS

D. B. Everett, J. S. Fleming, R. W. Todd, J. M. Nightingale, "A Prototype Gamma Camera Using the Compton Effect", *Proceedings of the Conference on the Applications of Electronics in Medicine*, Southampton, Hants, England, (Apr. 6-8, 1976), pp. 371-378, esp. p. 372.

R. W. Todd, J. M. Nightingale, D. B. Everett, "A Proposed Gamma Camera", *Nature*, vol. 251, (Sep. 13, 1974), pp. 132-134.

D. Doria and M. Singh, "Comparison of Reconstruction Algorithms for an Electronically Collimated Gamma Camera", *Abstracts of Papers*, IEEE 1981 Nuclear Science Symposium, Oct. 21-23, 1981.

"The Fan Beam Camera", *Physics of Medical Biology*, 1975, vol. 20, No. 3, pp. 489-491.

*Primary Examiner*—Janice A. Howell
*Assistant Examiner*—Constantine Hannaher
*Attorney, Agent, or Firm*—Sewall P. Bronstein

[57] ABSTRACT

A gamma radiation camera and a method are disclosed for creating an image of the radiation density of a source of photons. The camera comprises a detecting device made with solid-state material capable of generating electron-hole pairs as a result of collisions between photons and such material. The camera further includes an identifying device which identifies an ordered pair of said collisions in which both collisions result from a common photon. The camera further includes apparatus for determining an image of said source of common photon from the locations of the collisions of, and the number of electron-hole pairs generated by said ordered pair of collisions.

The apparatus for determining an image determines a collision line between two collisions of an ordered pair, and determines the angle of Compton scattering relative to the collision line which occurs at a first of the collisions of such a selected pair. In a preferred embodiment the gamma camera includes a parallel plate collimator placed between the detecting device and the position at which the source of photons is to be located. In such a preferred embodiment, the gamma camera further includes a second line determining device for determining a second line parallel with the collimation plane which forms the determined Compton scattering angle with the collision line at the location of the first collision of the selected pair.

42 Claims, 12 Drawing Figures

COMPTON SCATTERING GAMMA RADIATION CAMERA AND METHOD OF CREATING RADIOLOGICAL IMAGES

FIELD OF THE INVENTION

This invention relates to gamma radiation cameras used to create images of radioactive sources, such as radioactively labeled tissues within a human body, which emit gamma rays or X-rays

BACKGROUND OF THE INVENTION

The use of gamma radiation cameras is well known in the prior art. Such cameras have been extensively used in the field of nuclear medicine for the purpose of producing images of specified types of tissue within the human body. Radioactive nuclides of atoms such as thallium or 99m-technetium are made part of pharmaceutical chemicals which attach themselves to specified human tissues, such as bone tissue, muscle tissue, or blood tissue. Once the radionuclide-labeled chemical has been introduced into the body, and has had time to attach itself to the tissue to which it has a specific attraction, a gamma camera can be used to form an image of the resulting distribution of radioactivity. An important advantage of this diagnostic technique is that it permits noninvasive investigation of a variety of conditions of medical interest. For example, by injecting into a patient a radioactively tagged chemical which attaches to muscle tissue and by forming an image of the resulting radiation emitted from the various parts of a patient's heart, it is possible to determine which parts of that heart are receiving blood, as is required for heart tissue to remain healthy.

The gamma radiation camera was first developed by H. O. Anger in the late 1950's. His camera uses a large sodium iodide (NaI) scintillator crystal which emits visible light when struck by gamma ray or X-ray photons. A pinhole or a parallel hole collimator is placed between the scintillator crystal and the source of radiation to be imaged. On the opposite side of the scintillator crystal a matrix of photo-multiplier tubes is spaced a slight distance from the crystal, so that the relative amounts of light detected by the various photo-multiplier tubes enables a determination of the location within the crystal at which a scintillation resulting from the collision of a gamma ray or X-ray occurs. The pinhole causes the image of the radiation source to be focused on the surface of the scintillator crystal in a manner analogous to the operation of a pinhole camera. When a parallel hole collimator is used with such a scintillation crystal, most of the photons which reach the crystal are traveling generally perpendicularly to its surface and thus there is a correlation between the location at which such photons hit the scintillator and the position from which they are emitted.

Although the Anger camera represented a great advance in the field of nuclear medicine, it has several disadvantages. A first is that its energy resolution is normally limited to approximately ten to fifteen percent, which prevents it from distinguishing properly between primary photons emitted directly by a radioactive nuclide, which have the full energy of photons associated with that nuclide, and secondary photons emitted as a result of the Compton scattering of such primary photons. Such secondary photons have less energy than primary photons because of the energy lost in Compton scattering. Radiation images produced by cameras which can not distinguish between primary and secondary photons indicate many points as being sources of primary radiation which are only points at which primary photons have undergone Compton scattering, and thus such images are undesirably blurred.

Another problem associated with Anger type gamma cameras is that their use of pinholes or parallel hole collimators greatly reduces the number of photons emitted by radioactive sources which are able to hit scintillators. As a result it is necessary either to use large dosages of radioactive chemicals or long exposure times in order for a sufficient number of photons to be counted by the camera to produce a proper image. A further problem associated with such cameras is their low resolution. Even the best Anger cameras have a resolution of one to one and one half centimeters at ten to twelve centimeters from their pinhole or parallel hole collimator.

A gamma camera has been developed which uses a solid-state detector in conjunction with a parallel hole collimator. Such a camera is disclosed in U.S. Pat. Nos. 4,047,037 issued to Schlosser et al. and 4,055,765 issued to Gerber et al. This camera, instead of using a sodium iodide scintillator crystal, uses a solid-state detector made of the semiconductor germanium. When a photon hits an atom of germanium in such a detector, the collision creates electron-hole pairs. The germanium crystals are relatively flat, and on one side they have one or more electrodes for attracting the electrons and on the other side they have one or more electrodes for attracting the holes so produced. The electrodes on one side of the crystal determine the location of that collision along one axis and the electrodes on the opposite side determine the location of that collision along a perpendicular axis. The device also includes circuitry for determining the amount of electrons or holes that are released in any given collision. As a result, the device is capable of indicating an x position, a y position, and an energy associated with each photon collision which takes place with its semiconducting crystal. This semiconducting detector is used in conjunction with a parallel hole collimator, so that there is a correspondence between the location at which a photon hits the detector and the location from which that photon has been emitted.

Solid-state gamma cameras of the type disclosed in the Schlosser et al. and Gerber et al. patents have a much higher degree of energy resolution than is possible with gamma cameras using sodium iodide detectors, enabling the rejection of most unwanted secondary photons. This is true because it takes only approximately 2.9 electron volts (ev) for an electron-hole pair to be created in a collision with germanium, whereas it takes approximately 300 ev, or one hundred times as much energy, to create a photon of visible light in a collision with a NaI scintillation crystal.

Unfortunately the use of parallel hole collimators in the gamma cameras disclosed in the Schlosser et al. and Gerber et al. patents lets only a very small percent of the photons emitted by radiation sources through to their detectors, and thus either high radiation doses or long exposure times are required for use with such gamma cameras. In order to reduce the negative impact of their parallel hole collimators o the number of photons which reach their detectors to a reasonable level, gamma cameras of the type disclosed in the Schlosser et al. and Gerber et al. patents normally use collimators which are no more than two and one half centimeters thick. As a result, the resolution of such cameras at a distance of ten to twelve centimeters is usually worse than one centimeter.

A gamma camera which operates on a somewhat different principle was described in Session 2B-3 of the 1981 IEEE Nuclear Science Symposium, which took place at the Sheraton-Palace Hotel, in San Francisco, Calif., on Oct. 21st through 23rd, 1981. This session, entitled "Comparison of Reconstruction Algorithms for an Electronically Collimated Gamma Camera" was authored by D. Doria and M. Singh of the University of Southern California. The electronically collimated gamma camera referred to in that session has a flat sodium iodide scintillation crystal and associated photomultiplier tubes, like an Anger camera, together with a solid state detector of the type described in the Schlosser et al. and Gerber et al. patents, referred to above. The flat solid-state detector is placed parallel to the scintillation crystal and between that crystal and the source of radiation. If a photon undergoes Compton scattering with the solid-state detector and then collides with the camera's scintillator, the solid-state detector indicates the energy and location of the Compton scattering and the scintillator indicates the location of the scintillation collision. From this information and a knowledge of the expected energy of the gamma rays emitted from the source of radiation, the directional line which the photon travels between its collisions in the solid-state detector and in the sodium iodide crystal and the angle of Compton scattering at the collision in the solid-state detector can both be calculated, defining a cone of possible paths of the gamma ray before its collision with the solid-state detector. Such a cone has the location of Compton scattering in the solid-state detector as its tip, the translation line between the locations of the Compton scattering and the scintillation as its axis, and the angle of Compton scattering as its opening angle, i.e. the acute angle between the axis and wall of the cone.

Unfortunately, because the electronically collimated gamma camera only determines a possible cone from which each gamma ray it detects could have come, it requires the use of tomographic techniques, such as those described in the Session 2B-3, mentioned above, to generate a two dimensional image. Such tomographic techniques, which attempt to locate the origin of photons by finding the intersections of the cones of possible paths calculated from different collisions, require considerable computation and a great number of photons to be detected in order to give an image of reasonable quality. In addition, although the solid-state detector of the electronically collimated gamma camera provides relatively good energy resolution, the scintillation crystal used in such a device does not. For this reason the electronically collimated gamma camera does not have the ability to accurately distinguish between primary photons emitted directly by the source of radiation to be imaged and unwanted secondary photons emitted after Compton scattering.

SUMMARY OF THE INVENTION

The present invention provides a gamma camera and a method for creating an image of the radiation density of a source of photons located in a predetermined position relative to said camera. The camera includes detecting means comprising a solid-state material capable of generating electron-hole pairs as a result of collisions with photons. The detecting means includes means for determining the time, location and energy dissipated in a collision between a photon and said material. The camera also includes identifying means for identifying as ordered pairs those pairs of such collisions in which both collisions result from a common photon. The camera further includes means for determining an image of the source of photons from the locations of the collisions of, and the number of electron-hole pairs generated by at least one collision of, a plurality of such ordered pairs.

In a preferred embodiment the detecting means determines the time, location, and energy of collisions between that detecting means and photons by sensing the occurrence, location and number of electron-hole pairs, respectively, generated by each such collision. The detecting means further comprises means for determining the time, location and energy of each of two collisions which result from a common photon. The identifying means includes selecting means for choosing as an ordered pair a selected pair of such collisions, which selecting means includes means, responsive to the time of such collisions indicated by the detecting means, for selecting a pair of such collisions which occur at substantially the same time, indicating that the ordered pair of collisions results from a common photon. The means for determining an image comprises first line determining means, responsive to the selecting means and to the location of collisions indicated by the detecting means, for determining a collision line between the collisions of an ordered pair. In addition, the means for determining an image comprises angle determining means, responsive to the energy of at least one of the collisions of an ordered pair of collisions as indicated by the detecting means, for determining the angle of Compton scattering relative to the collision line determined by the first line determining means which occurs at a first of the collisions of an ordered pair. The means for determining an image further includes means for forming an image of said source using the location of the first collision, the collision line, and the angle of Compton scattering.

In a preferred embodiment the gamma camera further includes a parallel plate collimator placed between the detecting means and the position in which the source of photons is to be placed during imaging, so that the substantial majority of photons which reach the detecting means from the source of photons are traveling generally parallel to a known collimation plane. Such a gamma camera further includes second line determining means for determining a second line parallel with the collimation plane which forms the Compton scattering angle with the collision line at the location of the first collision of said ordered pair.

In a preferred embodiment the gamma camera further includes means for preventing a pair of collisions from being selected as an ordered pair unless the energy associated with one of those collisions indicates that the photoelectric absorption of a photon has occurred and unless the sum of the energies associated with that pair is within a predetermined range.

In a preferred embodiment the detecting means includes at least two detectors, each made of a semiconducting material, and each used for indicating the time, location, and energy of collisions between it and photons. These detectors are oriented relative to each other so that a photon produced in a collision detected in one of such detectors can produce a collision which is detected in another of the detectors. In a preferred embodiment each of the detectors includes a generally plate-shaped portion comprised of semiconducting material. One surface of each plate-shaped portion has attached thereto at least one electrode for determining the position of collisions along a first direction in the plane of that surface. The other, opposite, surface of each plate-shaped portion has attached thereto at least one electrode for determining the position of collisions along a second direction in the plane of that other surface. In one arrangement, two of such detectors are positioned relative to each other and to the position in which the source of photons is to be placed during imaging so that the planes of the plate-shaped portions of each of the two detectors intersect at an angle which faces the source of photons and so that a photon from the source can have a collision with either of the two detectors, undergo a Compton scattering, and have the resulting photon collide with the other of the two detectors.

According to another embodiment of the invention, the detecting means includes first and second separate detectors, each comprising semiconducting material, the first of which comprises a semiconducting material having a lower average atomic weight than the second. The first and second detectors are positioned relative to the position in which the source of photons is to be placed during imaging so that photons emitted directly from the source are more likely to hit the first detector than the second detector and so that photons resulting from Compton scattering in the first detector can collide with the second detector. Preferably, a majority of the atoms of the semiconducting material of the first detector are of silicon and a majority of the atoms of the semiconducting material of the second detector are of germanium. More preferably, the first detector is at least one and a half times thicker in the direction in which photons emitted directly from the intended source of photons pass into that first detector than the second detector is thick in the direction in which most of the photons emitted by Compton scattering from the first detector pass into that second detector. The first detector preferably has a plate-shaped portion which includes a target portion in which a substantial majority of the collisions between photons from the source of photons and the first detector are intended to take place, and the second detector preferably comprises four plate-shaped portions, one located perpendicularly to the plate-shaped portion of the first detector along each of four sides of a rectangle which surrounds the target portion of the first detector.

DESCRIPTION OF THE DRAWINGS

These and other aspect of the present invention will become more clear upon reading the following description of the preferred embodiments in conjunction with the accompanying drawings in which.

DETAILED DESCRIPTION OF PREFERRED EMBODIMENTS

Figure 1:
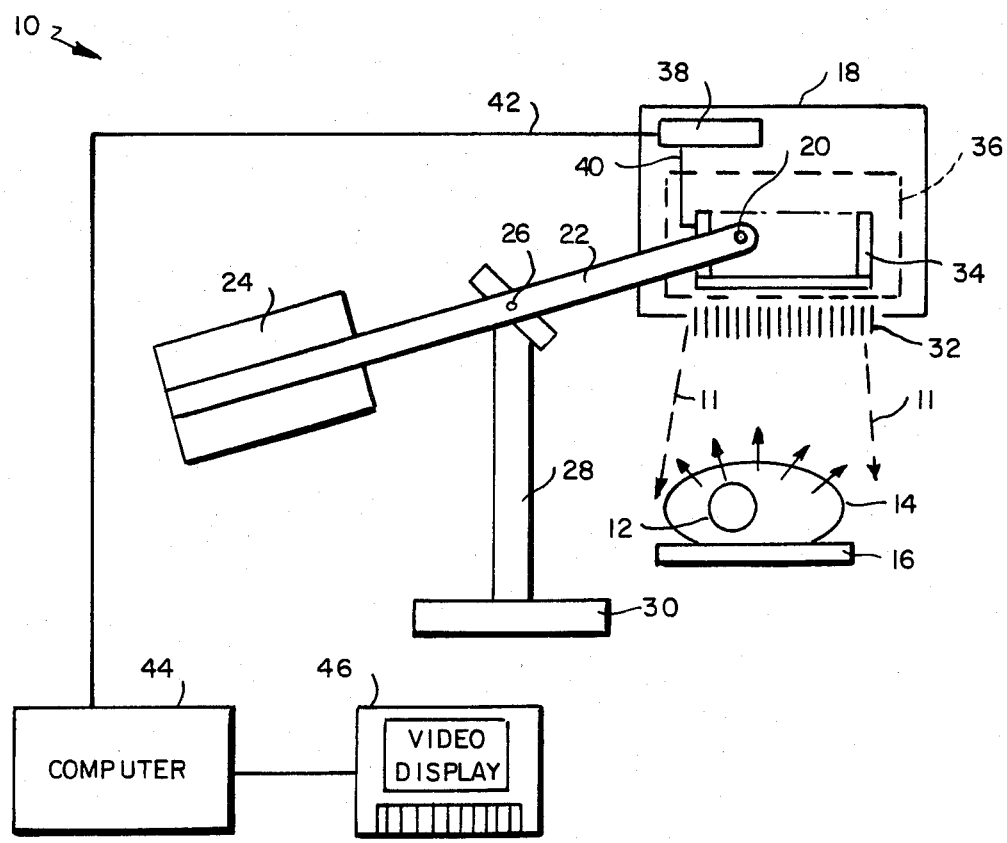
FIG. 1 is a schematic diagram of a gamma camera according to one embodiment of the present invention.

Referring now to FIG. 1 a simplified representation of a gamma camera 10, according to one embodiment of the present invention, is shown. Gamma camera 10 is used for producing an image of a source of radiation 12 placed in a predetermined source position indicated by the space between dotted lines 11 relative to camera 10. For example, source 12 can be a radioactively labeled human heart, located within a subject 14 placed upon a supporting table 16.

Gamma camera 10 includes a head portion 18, which is pivotally supported at pivot 20 from a beam 22. Beam 22, which carries a counterweight 24, is pivotally supported at pivot 26, in a dual axis gimbal fashion from an upstanding support 28. Support 28 is fixedly attached to and extends from a base member 30.

Head 18 of gamma camera 10 includes a parallel plate collimator 32 and solid-state detecting means 34. Parallel plate collimator 32 is located between detecting means 34 and the predetermined source position within the space defined by dotted lines 11. A source of photons 12 is to be placed in said predetermined position when an image of that source is to be made. Detecting means 34 is located within a cryogenic cooling compartment 36, indicated by the dotted lines at 36, which is used for the purpose of reducing the thermal noise in solid-state detector 34. Also located within head portion 18 of gamma camera 10 are interface electronics 38 which are connected to the solid-state detecting means 34 by means of connections represented at 40 and which are connected by means of connections represented at 42 to a programmable computer 44. Programmable computer 44 has as an output device a videographic display unit 46, upon which images produced by gamma camera 10 can be seen. The image produced by camera 10 can also be printed by means of graphic printing devices of a type well known in the computing arts.

Figure 2:
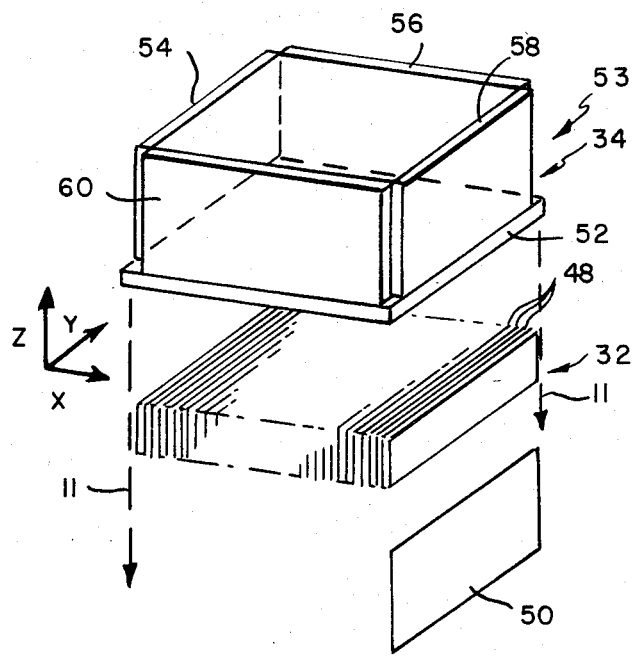
FIG. 2 is an exploded, perspective view of solid-state detecting means and a parallel plate collimator used in the embodiment of the invention shown in FIG. 1.

Referring now to FIG. 2, a more detailed representation of the geometry of parallel plate collimator 32 and detecting means 34 is shown. Parallel plate collimator 32 is comprised of a plurality of parallel plates 48, each of which is parallel to a known collimation plane 50. These collimation plates are made from a material having a high density and atomic number such as tungsten, tantalum, or lead to decrease the chance that photons will pass through such plates. Each of the plates 48 is approximately thirty centimeters long in the direction indicated by the arrow Y, approximately five centimeters wide in the direction indicated by the arrow Z, and approximately one quarter millimeter thick in the direction indicated by arrow X, as shown in FIG. 2. The plates of collimator 32 are spaced with their centers approximately two millimeters apart in the direction X shown in FIG. 2. Because of the two millimeters spacing and five centimeter width of the collimator plates, the substantial majority of photons which reach detecting means 34 through collimator 32 are traveling generally parallel to collimation plane 50.

Solid-state detecting means 34 is comprised of a first detector 52 and a second detector 53. Second detector 53 is made of four sides, 54, 56, 58 and 60 (hereinafter referred to collectively as 54–60). First and second detectors 52 and 53 are each made of semiconducting material and are each designed for determining the time, location, and energy of collisions between that detector and photons by sensing the occurrence, location and number of electron-hole pairs, respectively, generated by each such collision. First detector 52 and sides 54–60 of second detector 53 each comprise a generally plate-shaped structure comprised of semiconducting material. As used herein "plate-shaped" means a geometric shape having a relatively thin cross section or depth compared to the dimensions of its two opposing major planar surfaces. One surface of each of these plate-shaped structures has attached to it at least one electrode for determining the position of collisions with photons along a first direction in the plane of that surface. The other, opposite, surface of each plate-shaped structure has attached to it at least one electrode for determining the position of collisions with photons along a second direction in the plane of that other surface, which second direction is preferably perpendicular to the first direction.

Figure 3:
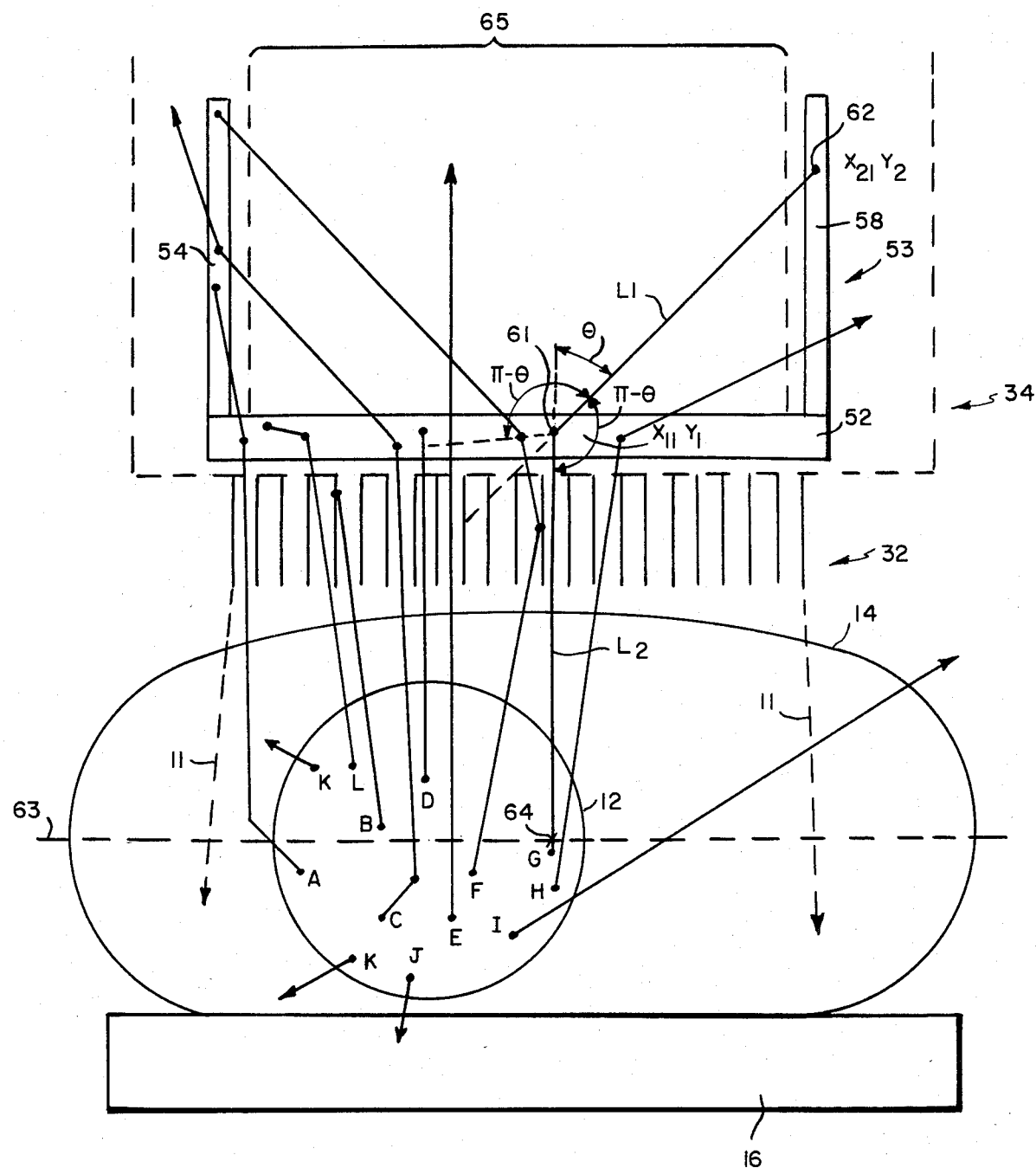
FIG. 3 is a simplified schematic representation of the solid-state detecting means and the parallel plate collimator of the embodiment of the invention shown in FIGS. 1-2 including a source of radiation emitting various photon paths.

Referring now to FIG. 3, there is shown a simplified cross section of collimator 32, first detector 52, sides 54 and 58 of second detector 53, and a subject 14 that has a radioactive source 12, such as a human heart, located within it. Also shown are a plurality of photon paths, emitted from points A–L within source 12.

In order to best understand these photon paths it should be remembered that photons can interact with semiconductors in basically three ways. The first is Compton scattering, in which a first photon collides with an atom of the semiconductor and is converted by the collision into a second photon emitted by the collision at an angle varying between zero and one hundred eighty degrees with the original path of the first photon. A Compton scattering collision causes the emitted photon it produces to have less energy than the incident photon which causes the collision. It also causes electron-hole pairs to be generated near the site of the collision in a number that is in direct proportion to the energy difference between the incident and the emitted photons. This energy difference, or loss, is a known function of the angle of Compto scattering. The second type of collision which a photon can have with a semiconductor is photoelectric absorption, which results in the photon being stopped by the collision and its entire energy being converted into electron-hole pairs. Thus when photoelectric absorption takes place the energy of the photon which has been absorbed can be determined by detecting the number of electron-hole pairs generated. The third type of collision which can occur between photons and a semiconductor is pair production, which results in the absorption of the photon and the conversion of its energy into the production of an electron-positron pair. However, pair production does not occur below an energy of 1.02 MeV, and thus is of little concern in gamma cameras, such as gamma camera 10, which are generally designed to operate with gamma ray or X-ray photons in an energy range of 50 to 511 keV.

Gamma camera 10 creates an image of radioactive source 12 by calculating the incident path of photons which strike its solid-state detecting means 34. It makes such a calculation only for those photons which result in a so-called "good events", which provides the camera with the information necessary to accurately calculate the incident path of such photons. A good event occurs when a photon, such as that shown originating at G in FIG. 3, undergoes a Compton scattering collision 61 which is detected in first detector 52 and the resultant photon emitted by that first collision is photoelectrically absorbed in a second collision 62 which is detected in second detector 53. As is described below in greater detail, from the position $X_1$, $Y_1$ of first collision 61 determined by first detector 52 and the position $X_2$, $Y_2$ of second collision 62 determined by the second detector 53, it is possible to calculate a collision line $L_1$ between the locations of the first and second collisions. As is also described below in greater detail, from the energy $E_1$ of the first collision and the energy $E_2$ of the second collision, detected by first and second detectors 52 and 53, respectively, it is possible to determine the angle of Compton scattering, $\theta$, which occurs at the first collision according to the formula:

$$\theta = \arccos\left(1 + \frac{511 \text{ keV}}{E_1 + E_2} - \frac{511 \text{ keV}}{E_2}\right) \quad \text{(Equation 1)}$$

Once the location of first collision 61, the collision line $L_1$ and the Compton scattering angle $\theta$ have been determined, it is possible to define a cone which represents all the possible incident paths which the photon which caused the first collision might have taken. This cone has the location of first collision 61 as its tip, since it is known that the incident path ended at that location. The cone also has the collision line $L_1$ as its axis and $\theta$ as its opening angle, that is, the acute angle between the axis and the wall of that cone, since it is known that the incident path formed an angle $\pi - \theta$ with the path $L_1$ of the photon emitted in the first collision.

Once such cones have been determined for many good events it is possible, using tomographic techniques, to determine from the intersections of such cones, an image of the source of radiation. However, in the embodiment of the invention shown in FIGS. 1, 2, and 3, such tomographic techniques are not required, because any photon which passes through collimator 32 and strikes first detector 52 is traveling generally parallel to collimation plane 50. Thus by finding the line of intersection $L_2$ which the plane of collimation that passes through the point of a first collision makes with the cone of possible photon paths defined by the location of the first collision, the collision line $L_2$ and the Compton scattering angle $\theta$, it is possible to calculate the incident path of the photon which gave rise to the first collision of a good event. Then, by finding the intersection of the line $L_2$ with a predetermined object plane 63 which is parallel to first detector 52 and is located at a selected distance from the collimator 32, it is possible to determine a point 64 having coordinates $X_0$ and $Y_0$ in that plane. By calculating a large number of such points $X_0$, $Y_0$ each associated with a good event, it is possible for the gamma camera in accord with the present invention to construct a relatively accurate image of a source of radiation.

As is described below in greater detail, camera 10 includes selecting means for choosing from among the many collisions which occur with detecting means 34 those which result in good events enabling accurate calculation of the direction from which photons are emitted by a radioactive source. Such selecting means include means for selecting as a good event only a pair of collisions which resulted from a common photon, the first of which is a Compton scattering caused directly by the common photon and the second of which is a photoelectric absorption caused directly by the photon emitted by the Compton scattering. These requirements for a good event are necessary for the calculation of the cone of possible incident photon paths associated with the first collision of a good event, as is discussed above.

The selecting means of camera 10 also includes means for causing a pair of collisions to be selected as a good event only if the sum of the energies $E_1$ and $E_2$ detected at the first and second collisions, respectively, is within a predetermined range of plus or minus two percent of the known energy of photons emitted directly by the radioactive source being imaged. Although the photons emitted by a given radioactive nuclide have a known energy at the time of their primary emission, it is possible for such photons to undergo Compton scattering, which results in the emission of secondary photons at locations removed from the position of their primary emission, as is shown by the photon emitted at point A in source 12 of FIG. 3. Photons which have been emitted by such secondary emission are undesirable for use in producing an image of a radioactive source, because their origin can be far removed from the location of the radioactive source which the imaging process is attempting to determine. Fortunately the energy of secondary photons emitted by such Compton scattering is less than that of primary photons emitted directly by a radioactive source. Thus by accurately determining the energy of a photon which causes the first collision of an event, as indicated by the sum of the energy $E_1$ of Compton scattering and the energy $E_2$ of photoelectric absorption associated with that event, it is possible to determine whether or not that photon is a desirable primary photon or an undesirable secondary photon. Solid-state detectors 52 and 53 of camera 10 have a very high energy resolution compared to sodium iodide scintillators of the type which have traditionally been used in Anger cameras. With the energy resolutions possible with such solid-state detectors, it is possible to select against photons which have been emitted as a result of any significant scattering.

Because it is necessary to determine the total energy of the photon which causes the first collision of an event in order to determine if that photon is a primary or a secondary photon, it can be seen why the second collision of a good event must be a photoelectric absorption. If it were not, it would be possible for a sequence of related photons, such as that originating at point C in FIG. 3, to undergo an unwanted Compton scattering before entering the gamma camera without that unwanted collision being detected. Because the collision in second detector 53 associated with such a sequence does not result in photoelectric absorption, it is impossible to tell the energy of the photon which caused the collision in detector 52, and thus it is impossible to tell whether that photon was a primary photon emitted directly from radioactive source 12 or whether it was an unwanted secondary photon emitted as a result of Compton scattering.

It is important to understand that only a small percent of the photons emitted by a source 12 results in good events of the type discussed above. A radiation source 12 normally emits photons in all directions with approximately equal probability, so that only the relatively small percent of the photons emitted by the source which are headed toward the camera 10 has a chance of being counted by it. Of these, somewhere in the vicinity of ninety to ninety-eight percent will be prevented from passing into first detector 52 because of collisions with parallel plate collimator 32. However, even though collimator 32 greatly reduces the number of photons which can be counted by camera 10, it nevertheless lets many more photons enter the detecting means of that camera than would the pinhole focusing devices or the parallel hole collimator traditionally used in gamma cameras of the prior art.

Of those photons which do reach first detector 52, many do not result in good events. Some, such as the photon emitted from the point E in FIG. 3, pass directly through first detector 52 and do not give rise to any collisions at all, and thus are not even detected. Others, such as that shown being emitted from point D in FIG. 3, undergo photoelectric absorption with the first detector, which prevents that photon from giving rise to any further collisions. Still others, such as that shown originating at point H in FIG. 3, undergo Compton scattering in first detector 52, but fail to have a collision in second detector 53, either because they pass through that detector without a collision, as shown in FIG. 3, or because their direction is such that they fail to pass into the second detector 53 at all. As has been discussed above, some photons, such as that shown originating at point C in FIG. 3, result in Compton scattering in both the first and second detectors, and thus the sum of the two collision energies $E_1$ and $E_2$ is not equal to the energy of the primary photon. It is also possible for a photon, such as that emitted from point L in FIG. 3, to undergo more than one collision within a given detector. Although it is possible to make an embodiment of the invention in which one semiconductor detector can detect both the first and second collisions of a good event, the preferred embodiments of the invention disclosed in this application have been designed to reject such events.

Because as many as a million points are required for the construction of a detailed radiological image, it is desirable that a gamma camera be designed so that as many of the photons emitted by a radioactive source as possible can be used in the calculation of an image. One of the major advantages of the present invention is that it enables a relatively high percent of the photons emitted by a radioactive source to be used in the calculation of an image, as compared to prior art gamma cameras.

Preferably, first detector 52 is made of silicon, whereas second detector 53 is made of germanium. Because silicon has a lighter atomic weight than germanium, a photon having an energy of 140 keV, the energy of photons emitted by the commonly used 99m-technetium, is ten times more likely to have a collision with silicon result in Compton scattering than in photoelectric absorption, whereas a similar photon entering a germanium crystal is about equally as likely to undergo photoelectric absorption as it is Compton scattering. Therefore, by making first detector 52 of silicon, the chances are greatly increased that collisions within it will result in Compton scattering, as is desired of the first collision of a good event. Similarly, constructing second detector 53 out of germanium, as opposed to silicon, greatly increases the chance that any collisions within it will result in a desired photoelectric absorption.

The likelihood of good events occurring in solid-state detecting means 34 is further increased by the geometry of that detector, which makes it much more likely for photons emitted directly from radioactive source 12 located in the desired source position in front of collimator 32 to hit the first detector than the second detector. The second detector is positioned relative to the first detector so that photons emitted by Compton scattering in the first detector are likely to hit it. This geometry, taken in combination with the use of silicon in the first detector and germanium in the second detector greatly increases the probability of good events. The geometry of the detector 34 is also designed to prevent the occurrence of so-called bad events, that is, collisions which are not usable as good events but which nevertheless undesirably occupy the time of detectors 52 or 53. For example, the plane of the plate forming first detector 52 is placed perpendicular to the path of photons which pass through the collimator 32, greatly increasing the chance that such photons will collide with it, whereas the planes of the plates forming sides 54–60 of second detector 53 are placed parallel to the average path of photons passing through collimator 32. This reduces the chance that photons, such as that originating at point E in FIG. 3, which pass through first detector 52 without a collision will collide with second detector 53, giving rise to a bad event that would merely waste the time of the circuitry used with detector 52 and 53. In addition to being placed generally parallel to the path of primary photons from source 12, sides 54–60 of second detector 53 are also placed to form a rectangle outside the central, or target, portion 65 of the first detector 52 in which the substantial majority of collisions between photons from source 12 and first detector 52 take place. Because sides 54–60 are not placed over target portion 65, relatively few of the photons which pass through first detector 52 without a collision hit any of the sides 54–60 and give rise to a bad event.

In camera 10, in which a parallel plate collimator 32 of the type shown in detail in FIG. 2 is used and in which first detector 52 is thirty centimeters by thirty centimeters by one centimeter and is made of silicon and sides 54–60 of second detector 53 are each thirty centimeters by fifteen centimeters by one half centimeter and are made of germanium, a radiation source approximately ten centimeters in front of the center of collimator 32 results in the generation of approximately four hundred fifty-eight good events per minute per microcurie of radioactive substance used, when the radioactive substance is 99m-technetium which emits 140 keV photons. The same camera results in approximately eight hundred seventy good events per minute per microcurie for a radioactive substance, such as 201-thallium chloride, which emits photons with an energy of approximately 83 keV. The higher count rate for a radioactive substance with a lower energy level results because more lower energy photons undergo Compton scattering at an angle large enough to cause them to hit sides 54–60 than do higher energy photons, and because a greater number of the photons emitted from first detector 52 by Compton scattering at such lower energies result in photoelectric absorption when they hit second detector 53 than at higher energies.

Increasing the thickness of first detector 52, which is made of silicon, increases the count rate because it decreases the number of photons which pass through it without a collision. It has been found that similarly increasing the thickness of sides 54–60 of second detector 53, which are made of germanium, does not yield a great an improvement in the count rate, and thus is not generally justified in view of the high cost of germanium crystal. Thus it is preferred that the plate of the first detector be at least one and a half times thicker than the plates of the second detector. In fact, if the thickness of first detector 52 is increased to two centimeters, the count rate of good events increases to eight hundred counts per minute per microcurie at 140 keV and one thousand five hundred counts per minute per microcurie at 83 keV.

These count rates represent a significant improvement over count rates in the vicinity of two hundred fifty counts per minute or less which are typically obtained with Anger type scintillation cameras for photons in the energy range of 80 to 140 keV. As a result of the higher count rates per microcurie which can be obtained with the present invention, it is possible to make images of equal or better quality than are obtainable in the prior art with either a lower dosage of radioactive chemicals, a lower exposure time, or a combination of both lower radioactive dosage and exposure time. For example, the count rate of four hundred fifty-eight counts per minute achievable with 140 keV photons when first detector 52 is made of silicon one centimeter thick makes it possible to produce an image almost twice as fast as is normally achievable with current Anger type scintillation cameras. Using 83 keV photons enables that device to make an image over three times faster than is commonly achievable with current Anger type scintillation cameras.

Another advantage of the present invention is that its resolution is considerably better than that normally achievable with current Anger cameras. Even though the more advanced Anger cameras claim an intrinsic resolution of approximately two millimeters for a source of radiation which is located next to their parallel hole collimators, such cameras' resolution drops to between one to one and one half centimeters for a source of radiation which is ten to thirteen centimeters away from such a collimator, as are many of the parts of the human body during imaging. Similar resolutions of approximately one to one and a half centimeters are obtainable at such distances from Anger cameras which use a pinhole to focus the photons which they record. With the embodiment of the invention shown in FIG. 2, however, resolutions of approximately four millimeters can be obtained from a radioactive source which is at a distance of ten to thirteen centimeters from collimator 32, and this applies to both planar directions. It is readily seen that this increase in resolution of between two to four times along each axis which is obtainable with the present invention represents significant improvement in the art.

Figure 4:
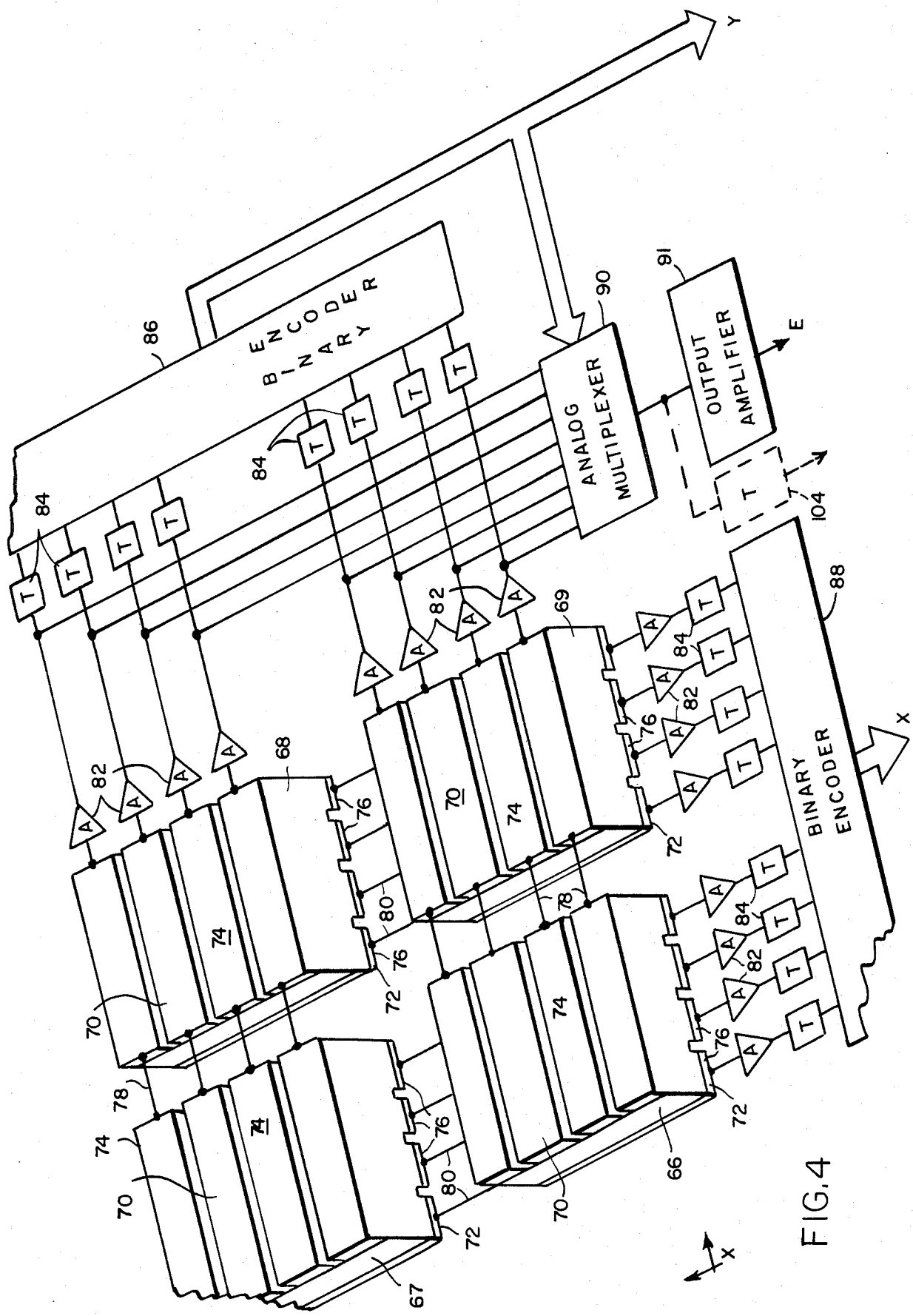
FIG. 4 is a simplified schematic diagram of a plate-shaped portion of the solid-state detecting means used in the present invention and of the circuitry used to provide indications of the time, location and energy of photon collisions with that plate-shaped portion.

Because it is presently impractical to make individual semiconductor crystals as large as desired for any of the plates of first or second detectors 52 or 53, it is necessary to make each of those plates out of a composite of smaller crystals. For this reason first detector 52, which is thirty centimeters by thirty centimeters by one centimeter, is made up of eighteen separate silicon crystals, each five centimeters by ten centimeters by one centimeter, arranged in a three by six matrix. Each of the four sides 54–60 of second detector 53, which are thirty centimeters by fifteen centimeters by one half centimeter, is made of a three by three matrix of germanium crystals, each of which is five centimeters by ten centimeters by one half centimeter. FIG. 4 is a simplified rendition of a two by two crystal matrix used to show how the individual crystals of detectors 52 and 53 are connected and how they can generate information concerning the time, location, and energy of collisions with photons.

The simplified semiconductor structure shown in FIG. 4 is made up of four semiconducting crystals 66–69, each of which is made of the same type of relatively pure, intrinsic semiconducting material, silicon or germanium. The upper surface 70 of each such crystal is doped with an impurity to give it a P type semiconducting characteristic, and the bottom surface 72 of each such crystal is doped with an impurity to give it an N type semiconducting characteristic. Then top and bottom surfaces 70 and 72 of crystals 66–69 are etched to create a plurality of separate, parallel P type electrodes 74 on upper surface 70 of each crystal and a plurality of separate, parallel N type electrodes 76 on bottom surface 72 of each crystal, with electrodes 74 running in a direction perpendicular to electrodes 76. Crystals 66–69 are then placed in a holder (not shown) made of an insulating material such as nylon. Such a holder holds crystals 66–69 in close proximity to each other with P type electrodes 74 and N type electrodes 76 of adjacent crystals aligned with each other, respectively. The holder has, built into its surfaces which press against the top of crystals 66–69, a plurality of separate connections 78 which connect each P type electrode 74 on one crystal with the P type electrode 74 which is aligned with it on an adjacent crystal. Similarly, the holder has a plurality of connections 80, built into its surfaces which press against the bottom of crystals 66–69, which connect aligned N type electrodes 76 contained on adjacent crystals. Thus the composite structure created out of semiconducting crystals 66–69 has a plurality of separate, aligned, interconnected P type electrodes 74 which run in the X direction and a plurality of separate, aligned, interconnected N type electrodes 76 which run in the Y direction shown in FIG. 4.

Each separate sequence of aligned, interconnected P type electrodes 74 and each separate sequence of aligned, interconnected N type electrodes 76 are connected at one end to a preamplifier 82. Each of these aligned, interconnected sequences of P type electrodes 74 is connected to a source of relatively negative voltage and each of the aligned, interconnected sequences of N type electrodes 76 is connected to a source of relatively positive voltage, by means which are not shown in FIG. 4. When a photon collides with one of the semiconducting crystals 62–68 electron-hole pairs are generated in a number proportional to the energy of the collision. Substantially all of the holes generated by such a collision are attracted to the nearest P type electrode 74 and substantially all of the free electrons generated are attracted to the nearest N type electrode 76. Experience has shown that due to the very small scattering of such free electrons and holes in directions perpendicular to the field created by the electrodes 74 and 76, it is very rare for the free electrons or holes created by a single collision to be split in any significant proportion between neighboring electrodes on one side of a crystal. As a result, the preamplifiers 82 which are connected to the P type electrode 74 and the N type electrode 76 which are nearest the collision generate a signal proportional to the number of holes and electrons produced as a result of such a collision, which number is directly proportional to the energy of that collision.

The output of each preamplifier 82 is connected to a threshold detector 84. Each threshold detector 84 is designed to produce a binary signal which is high only when the voltage produced at the output of its associated preamplifier is sufficiently high to indicate the detection of a photon collision. At all other times the output of the threshold detector 84 is low. The outputs of the threshold detectors 84 associated with P type electrodes 74 are fed into the input of a binary encoder 86. Similarly, the outputs of the threshold detectors 84 associated with N type electrodes 76 are supplied to the input of a binary encoder 88. Each of the binary encoders 86 and 88 produces a multibit digital signal which indicates which of its binary inputs has high signal. Thus when a photon collides with one of the semiconductor crystals 66–69, one of the aligned, interconnected sequences of P type electrodes 74 receives holes generated by the collision and causes its associated preamplifier 82 and threshold detector 84 to provide a binary high signal to encoder 86, which in turn produces as an output a binary signal indicating the location of that collision along the Y direction, as shown in FIG. 4. Similarly, after such a collision, one of the aligned, interconnected sequences of N type electrodes 76 receives electrons generated by the collision and causes its associated preamplifier 82 and threshold detector 84 to provide an input to binary encoder 88 which causes that encoder to produce a multibit output indicating the location of that collision along the X direction, as shown in FIG. 4.

The output of each of the preamplifiers 82 associated with P type electrodes 74 is connected to one input of an analog multiplexer 90. The multibit output of binary encoder 86 is supplied to the control input of that multiplexer, so that once encoder 86 determines that a given preamplifier 82 is producing a signal indicating the detection of a collision, the analog voltage produced by that preamplifier is selected for connection to the output of multiplexer 90. This selected voltage is supplied to an output amplifier 91, which amplifies that selected voltage and provides it as an output signal E which indicates the energy of the collision which has been detected.

The binary encoder 86 is designed to produce an error value if more than one threshold detector 84 supplies it with a high signal at once, and this error signal will prevent any of the voltages supplied to multiplexer 90 from being connected to the output of that multiplexer. As a result, if an undesired situation occurs in which two unrelated collisions occur in rapid succession or in which a photon released as a result of the Compton scattering in a first collision gives rise to a second collision within the same detector plate, the error signal generated by multiplexer 86 will prevent any voltage from being passed through multiplexer 90, which, in turn, will prevent the data produced by such an undesired plurality of collisions from being used by the gamma camera.

As stated above, the device shown in FIG. 4 is a simplification of the composite semiconductor devices used to form first detector 52 and sides 54–60 of second detector 53. In detectors 52 and 53 electrodes 74 and 76 are spaced with their centers approximately two millimeters apart. As a result, electrodes 76 which run along the bottom of first detector 52 can be aligned and registered with the similarly spaced openings between parallel plates 48 of collimator 32. Since first detector 52 is approximately thirty centimeters by thirty centimeters, there are one hundred fifty aligned, interconnected sequences of electrodes along both its top and bottom surfaces. Thus, there are one hundred fifty preamplifiers 82 and threshold detectors 84 associated with each of the two opposing major surfaces of that detector, and the binary encoders 86 and 88 must each have one hundred fifty inputs and an eight bit digital output to indicate the Y or X coordinates indicated by electrodes 74 and 76. Similarly, since each of the sides 54–60 of second detector 53 is approximately thirty centimeters by fifteen centimeters, one hundred fifty outputs will be associated with one of its major surfaces and seventy-five outputs will be associated with its opposite surface.

Because of the frequency with which electron-hole pairs are generated in germanium by thermal energy at room temperature, it is necessary to keep the second detector 53, which is made of germanium, in a low-temperature, preferably cryogenic, environment by cooling it with liquid nitrogen at a temperature of 77° Kelvin. This can be done according to methods well known in the cryogenic arts. Because it is necessary to provide cooling for the germanium detector, it is little trouble to provide such cooling to the first detector, which is made of silicon. However, it is not necessary to provide such cryogenic cooling for the first detector, because the energy of the conduction bands is considerably higher in silicon than in germanium, and thus the generation of electron-hole pairs in silicon by thermal energy is much less frequent at room temperatures.

Figure 5:
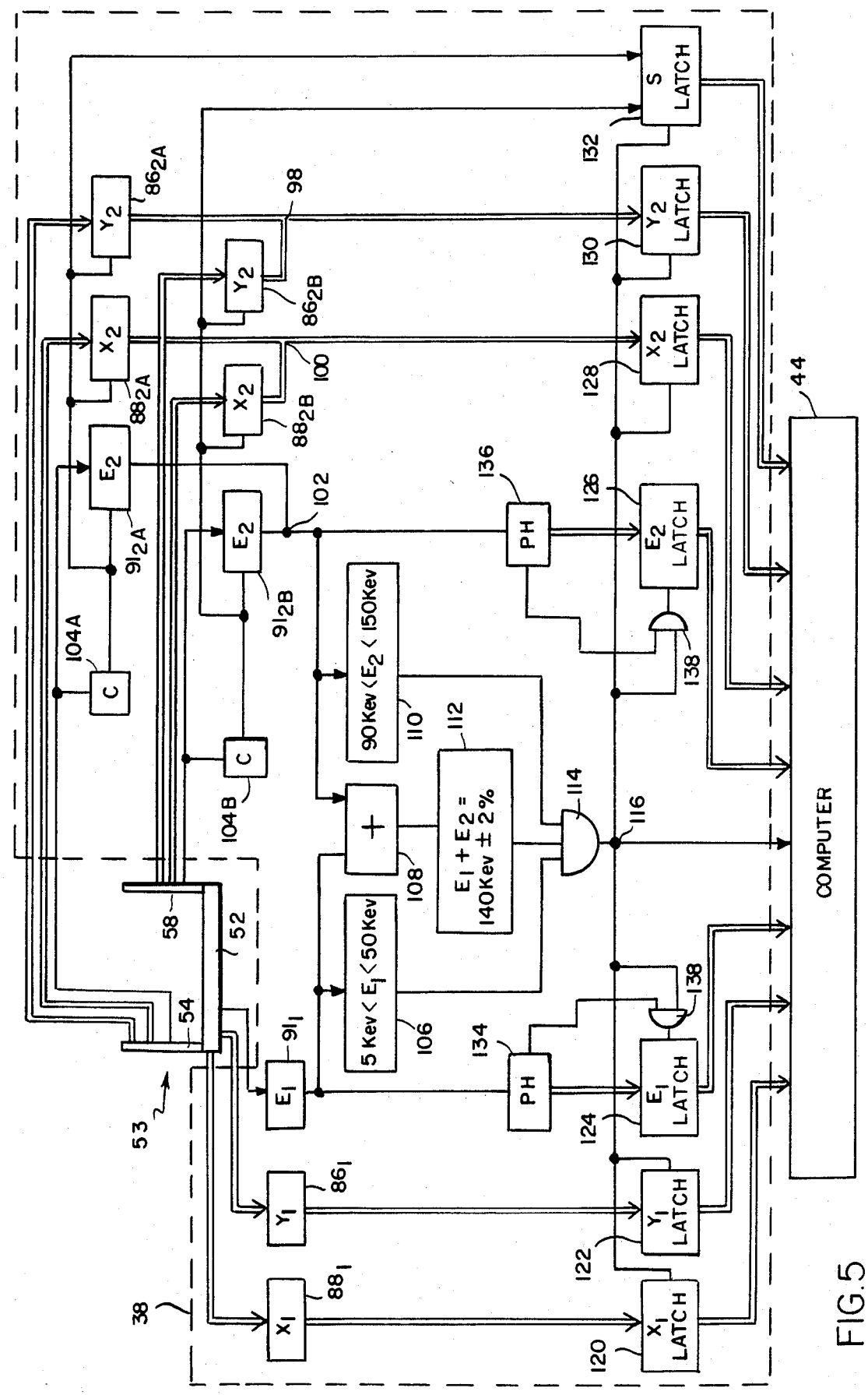
FIG. 5 is a schematic diagram of the circuitry used in the embodiment of the invention shown in FIGS. 1-2.

Referring now to FIG. 5, the electronics 38 of gamma camera 10 will be described. In this figure, first detector 52 is shown connected to binary encoders $86_1$ and $88_1$ and to output amplifier $91_1$, which correspond, respectively, to binary encoders 86 and 88 and output amplifier 91 shown in FIG. 4. Similarly, side 54 of second detector 53 is shown connected to binary encoders $86_{2A}$ and $88_{2A}$ and to output amplifier $91_{2A}$ and side 58 of second detector 53 is shown connected to binary encoders $86_{2B}$ and $88_{2B}$ and to output amplifier $91_{2B}$, which also correspond, respectively, to binary encoders 86 and 88 and output amplifier 91 of FIG. 4. For purposes of simplification, sides 56 and 60 of the second detector 53 and their associated outputs, which are similar in design and function to those of sides 54 and 58 are not shown in FIG. 5. Also for purposes of simplification, elements corresponding to preamplifiers 82, threshold detectors 84 and analog multiplexer 90 shown in FIG. 4 have been omitted from FIG. 5.

Each of the two Y coordinate binary encoders $86_{2A}$ and $86_{2B}$ of the second detector have their outputs connected at 98, each of the X coordinate binary encoders $88_{2A}$ and $88_{2B}$ of the second detector have their outputs connected at 100, and each of the output amplifiers $91_{2A}$ and $91_{2B}$ of the second detector have their outputs connected at 102. Each of these output devices $86_{2A}$, $86_{2B}$, $88_{2A}$, $88_{2B}$, $91_{2A}$ and $91_{2B}$ associated with second detector 53 have outputs which can be tri-stated by means of a control signal. As is well known in the electronic arts, when an output device is tri-stated, a large impedance is placed at its output which effectively separates its output from any signal contained within that device. As is shown in dotted lines in FIG. 4, a threshold detector 104 can be connected to the output of analog multiplexer 90 which generates a high output only when the output of multiplexer 90 indicates a collision has taken place in the semiconductor device associated with that multiplexer. In the circuitry shown in FIG. 5, sides 54 and 58 of the second detector each have such a threshold detector, $104_A$ and $104_B$, respectively, which produces a high signal when the energy output of that side indicates that a collision has been detected in it. The output of threshold detectors $104_A$ and $104_B$ are supplied to the tri-state control inputs of output devices $86_{2A}$, $88_{2A}$, and $91_{2A}$ (in the case of detector $104_A$) and $86_{2B}$, $88_{2B}$, and $91_{2B}$ (in the case of detector $104_B$). Thus each such threshold detector keeps the output devices to which it is connected tri-stated at all times except when the energy output associated with its corresponding side 54 or 56 indicates the detection of a collision. When such a collision is detected, the associated threshold detector temporarily ends the tri-stating of the output devices to which it is connected, causing the values within each of those output devices to be supplied to the connections 98, 100, and 102, respectively. This selective use of tristating reduces the noise at the connections 98, 100, and 102.

The output of the energy output amplifier $91_1$ is supplied to the input of a window comparator 106 and to one of the two inputs of a summing amplifier 108. The window comparator 106 produces a binary output which has a high level only if the output $E_1$ of amplifier $91_1$ indicates that the first detector 52 has detected a collision having an energy between 5 and 50 keV. This is the energy associated with the Compton scattering of a 140 keV photon emitted by 99m-technetium, a commonly used radioactive isotope. A minimum value of 5 keV is required by the window comparator 106 so that it will not be activated either by noise or by Compton scatterings in which the energy of the collision is very slight. It is undesirable for the apparatus to concern itself with Compton scattering which involves small energies, since it is difficult to accurately calculate the angle of such scattering from such small energies. It should be noted that if a gamma camera is being used with a radioactive source having photons of an energy other than 140 keV, such as a thallium isotope which emit photons with an energy of 83 keV, the boundary values of the window comparator 106, and all the other energy values specified in FIG. 5 should be altered to correspond with desired collision energies for the photons emitted by such a radioactive source.

The output of the energy amplifiers $91_{2A}$ and $91_{2B}$ which has been selected by its associated detector $104_A$ or $104_B$ is supplied through connection 102 to the input of a window comparator 110, which produces a binary output which is high only when the energy $E_2$ supplied to it is between 90 and 150 keV. This energy range is associated with the photoelectric absorption of photons which either have been emitted directly from a 140 keV radioactive source or have been emitted as a result of the Compton scattering of such a directly emitted photon. The energy signals $E_1$ and $E_2$, supplied to the inputs of summing amplifier 108 are added together in that amplifier and are then supplied to the input of a window comparator 112, which produces a binary output which has a high level only if the sum of $E_1$ and $E_2$ is within plus or minus two percent of the 140 keV energy associated with 99m-technetium photons. The outputs of window comparators 106, 110 and 112 are supplied to the three inputs of an AND gate 114, which produces a high output only if all three of those inputs are high at the same time. Because the output of comparator 106 is high only when the energy $E_1$ indicates that Compton scattering has occurred within first detector 52, because the output of comparator 110 is high only when the energy $E_2$ indicates that a photoelectric absorption has taken place in the second detector 53, and because the output of comparator 112 is high only when the sum of the energies $E_1$ and $E_2$ is within two percent of the 140 keV energy associated with a photon emitted directly from a 99m-technetium isotope, the AND gate 114 will only produce a high output when a good event is detected in which a photon emitted either directly from a radiation source or after only slight scattering causes Compton scattering in first detector 52 and the photon resulting from that Compton scattering results in photoelectric absorption in second detector 53.

The good event output 116 from AND gate 114, which is high only when a good event is detected by AND gate 114, is supplied as an interrupt input to computer 44. This interrupt informs computer 44 that a good event has been detected and that it should read the $X_1$, $Y_1$, $E_1$, $X_2$, $Y_2$, $E_2$ and $S_2$ values which define that event into a specified location, called the event stack, in the computer's memory, as will be described below. The good even output 116 is also supplied to the latching control inputs of latching devices 120, 122, 124, 126, 128, 130, and 132, which are associated respectively with the outputs of the $X_1$ binary encoder $88_1$, the $Y_1$ binary encoder $86_1$, the $E_1$ output amplifier $91_1$, the $E_2$ output supplied at connection 102, the $X_2$ output supplied at connection 100, the $Y_2$ output supplied at the connection 100, and the combined outputs $S_2$ of the detectors $104_A$ and $104_B$.

The $E_1$ output from amplifier $91_1$ and the $E_2$ output from connection 102 are each analog signals which are passed through pulse height analysis circuits 134 and 136, respectively. These circuits convert those signals into binary signals before they are supplied to the inputs of their respective latches 124 and 126. Pulse height analysis circuits 134 and 136 are of a type well known in the electronic arts. Each such circuit monitors the analog signal supplied to its input and picks the highest value of that signal and converts that highest value into a twelve bit binary signal. Because the values of the signals $E_1$ and $E_2$ are both transitory, it is desirable to take a reading of those signals at their highest point in order to get a signal which is proportional to the energy of the collisions which they indicate. The good event output 116 is supplied to the latching input of each of the latches 124 and 126 through a separate AND gate 138. The other input of each AND gate 138 is supplied from an output of the associated pulse height analysis circuits 134 or 136, which output goes high once the highest value of the signal supplied to that pulse height analysis circuit has been picked and produced as a binary output. The use of AND gates 138 prevents the latching of latches 124 and 126 until the output of their associated pulse height analysis circuits 134 and 136 is ready.

The outputs of the threshold detectors $104_A$ and $104_B$, in addition to being supplied to the tri-state control inputs of the output devices $86_{2A}$, $86_{2B}$, $88_{2A}$, $88_{2B}$, $91_{2A}$, and $91_{2B}$, are also supplied to the inputs of a binary latch 132. This latch 132 merely stores the values contained on each of the lines $104_A$ and $104_B$ at the time that a good event signal is generated at 116, so that the outputs of the threshold detectors $104_A$ and $104_B$, which indicate the side 54 or 58 of second detector 53 in which a collision has been detected, will be stored for reading by computer 44.

Figure 6:
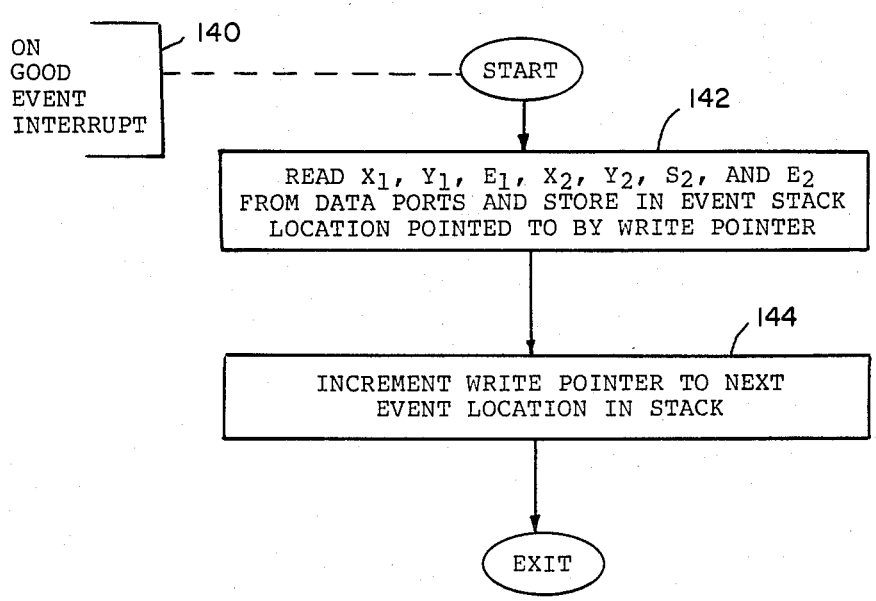
FIGS. 6 and 7 are block diagrams illustrating one embodiment of the computational steps used to create an image of a photon source for the camera of FIG. 5.
Figure 7:
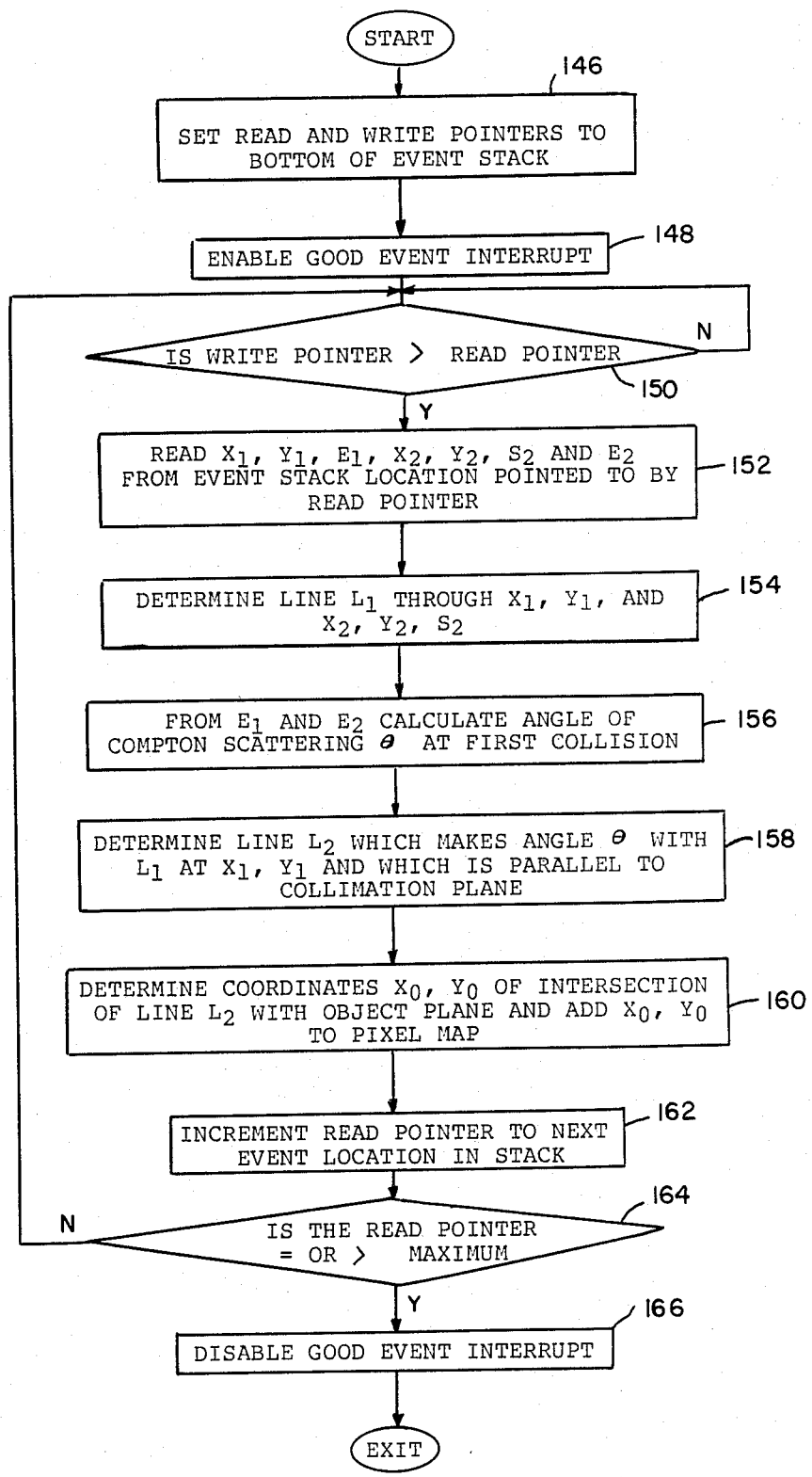

Referring to FIGS. 6 and 7, the program of computer 44 used by gamma camera 10 in forming an image of a radioactive source will be described. The good event output 116 is supplied to an interrupt input of computer 44, so that, when output 116 goes high, computer 44 is interrupted. When such a good event interrupt is generated, as is indicated at 140 in FIG. 6, computer 44 temporarily interrupts its performance of the program of FIG. 7, described below, and executes the subroutine shown in FIG. 6. The first step 142 of this subroutine causes the computer to read in the values of $X_1$, $Y_1$, $E_1$, $X_2$, $Y_2$, $S_2$, and $E_2$ which are stored in latches 120–132, shown in FIG. 5, and supplied to corresponding parallel I/O ports contained within computer 44. The computer reads the digital values associated with a good event from these parallel I/O ports and stores them in a sequence of addresses in a portion of its memor called the event stack. The values $X_1$, $Y_1$, $E_1$, $X_2$, $Y_2$, $S_2$, and $E_2$ associated with a given good event are stored in an event location within the event stack pointed to by a variable called the write pointer. This write pointer points to the first address within an event location at which the first piece of information associated with a given event is stored.

After the step 142 has been completed, the program advances to step 144 in which the write pointer is incremented so that it points to the beginning of the next event location in the memory of computer 44. This is done so that the next time a good event interrupt is generated the data associated with that next event will be stored at the next event location in the event stack. After step 144 has been completed, the program exits the interrupt program and the computer returns to performing whatever program it was executing before the interrupt was generated.

The main program which the computer 44 performs during the creation of a radiological image is shown in FIG. 7. The first step of this program, step 146, involves the setting of the write pointer described above, to the bottom of the event stack. It also involves the setting of a read pointer to the same address. The second step of this program, step 148, involves enabling the good event interrupt. This makes it possible for the computer to respond to an interrupt from output 116 and, thus, to perform the interrupt subroutine shown in FIG. 6. The interrupt is not enabled until the write pointer has been set, since the computer would not know at which address to store the data relating to a good event until that pointer has been set. Once step 148 has been performed, the computer advances to step 150 in which it determines whether or not the write pointer is greater than the read pointer. If the answer is no, the computer keeps looping until it is yes, because unless the write pointer is greater than the read pointer, there are not any events stored in the event stack which have not yet been read. Once the write pointer is greater than the read pointer, indicating that one or more events have been stored in the event stack which have not yet been read, the program advances to step 152.

At this step the program reads the values of $X_1$, $Y_1$, $E_1$, $X_2$, $Y_2$, $S_2$ and $E_2$ from the event stack location pointed to by the read pointer, and then it advances to step 154. At step 154, the computer determines a collision line $L_1$ which passes through the point indicated by the values $X_1$, $Y_1$ and the point indicated by the values $X_2$, $Y_2$ and $S_2$, which values have just been read from the event stack. Because the computer makes a simplifying assumption that collisions in the first detector occur midway between its two opposing major surfaces, the coordinates $X_1$ and $Y_1$ define the location of the point of the first collision in three dimensional space. Similarly, because the orientation of each of the sides 54-60 of the second detector 53 is known, because the computer assumes that all collisions in a given plate detector occur midway between its two opposing major surfaces, and because the value $S_2$ indicates in which of those plates a collision has taken place, the values $X_2$, $Y_2$ and $S_2$ similarly define the location of the second collision in three dimensional space. From this three dimensional information concerning the location of the first and second collisions, it is possible by well known geometric techniques to calculate the line which runs between those locations.

Since the first and second detectors have a thickness of one centimeter and one half centimeter, respectively, the simplifying assumption that all collisions occur midway between the two major surfaces of such detectors does generate some error. Although this error is not very large with detectors of a thickness of one centimeter or less, it can be substantially reduced by the introduction of timing circuitry which compares the time at which electrons are picked up by an electrode on one side of the crystal with the time at which holes are picked up by an electrode on the opposite side of the crystal in response to a given collision. By comparing these times it is possible to calculate the distance of such a collision from each of the two major surfaces of a semiconducting crystal, and thus to determine the location of such a collision in all three dimensions.

Once the line $L_1$ has been determined by step 154, the program advances to step 156, in which the angle of Compton scattering $\theta$, which takes place at the first collision of the good event is calculated from the energies $E_1$ and $E_2$ which have been read from the event stack in step 152. $\theta$ can be calculated from $E_1$ and $E_2$ because the angle of a Compton scattering is defined by the following equation:

$$\lambda_2 - \lambda_1 = \frac{h}{mc}(1 - \cos\theta) \quad \text{(Equation 2)}$$

where $\lambda_1$ is the wavelength of the photon which gives rise to the Compton scattering, $\lambda_2$ is the wavelength of the photon which is emitted as a result of the Compton scattering, h is Planck's constant, m is the rest mass of an electron, c is the velocity of light, and $\theta$ is the Compton scattering angle. Because the wavelength $\lambda$ of a photon is related to its energy E by the following equation:

$$\lambda = \frac{hc}{E} \quad \text{(Equation 3)}$$

the wavelength of the photon which gives rise to the first collision of a good event should be determined by the known energy of photons emitted by the radioactive source being used, which in the case of 99m-technetium is 140 keV. However, it is possible that the photon which has caused the first collision of a good event has undergone slight Compton scattering before its collision with the solid-state detecting means of a gamma camera. Therefore it is more accurate to define $\lambda_1$ as follows:

$$\lambda_1 = \frac{hc}{E_1 + E_2} \quad \text{(Equation 4)}$$

$E_1 + E_2$ should equal the energy of the photon which has caused the first collision of a good event. Due to the conservation of energy, all of the energy of that photon which is not lost as $E_1$ in the Compton scattering collision of a good event should be absorbed as $E_2$ in the photoelectric absorption of the event. Similarly, the wavelength $\lambda_2$ of the photon which is emitted as a result of the Compton scattering collision of a good event is given by:

$$\lambda_2 = \frac{hc}{E_2} \quad \text{(Equation 5)}$$

This is true because all of the energy of the photon emitted by the Compton scattering collision is lost as $E_2$ in the photoelectric absorption.

Substituting Equations 4 and 5 into Equation 2 gives the following equation which defines the angle of Compton scattering in terms of energies $E_1$ and $E_2$:

$$\frac{hc}{E_2} - \frac{hc}{E_1 + E_2} = \frac{h}{mc}(1 - \cos\theta) \quad \text{(Equation 6)}$$

This Equation 6 can be simplified to:

$$\cos\theta = 1 + \frac{mc^2}{E_1 + E_2} - \frac{mc^2}{E_2} \quad \text{(Equation 7)}$$

Since $mc^2$ equals 511 keV, Equation 7 can be rewritten in the following form (which is identical to Equation 1 listed above):

$$\theta = \arccos\left(1 + \frac{511 \text{ keV}}{E_1 + E_2} - \frac{511 \text{ keV}}{E_2}\right) \quad \text{(Equation 8)}$$

Using equation 8 it is possible from the values of $E_1$ and $E_2$ which have been read from the event stack to calculate the angle $\theta$ which is associated with that event.

Once step 156 has been completed, the program moves to step 158, which determines a second line $L_2$ which makes the angle $\theta$ calculated in step 156 with the collision line $L_1$ calculated in step 154 at the position $X_1$, $Y_1$ of the first collision and which is parallel to collimation plane 50. Because $L_1$, the angle $\theta$, $X_1$, $Y_1$ and the collimation plane 50 are all known, the line $L_2$ can be calculated by well known geometric techniques.

In general, two lines can be generated to have an angle $\theta$ with line $L_1$ in plane 50. However, only the line which points to the camera's field of view is selected for image construction. Events which generate two lines which are both in the camera's field of view will be rejected.

Once step 158 is completed, the program advances to step 160, which finds the coordinates $X_0$, $Y_0$ of the intersection of the line $L_2$ with the object plane 63, shown in FIG. 3, in which it is assumed that the source of radiation lies for purposes of creating an image. Although this assumption introduces some error into the image which is produced, this error is normally quite slight and thus does not present a major problem. Once the point $X_0, Y_0$ has been calculated for a given event, it is added to a pixel map in the computer which stores the sum of the points $X_0, Y_0$ which have been calculated and which forms an image of the radiological source. Such a pixel map can then be shown on a videographic terminal or it can be printed by means of a graphic printer.

After step 160 has been completed, the program moves on to step 162, in which the read pointer is incremented to address the next event location in the event stack. Then the program moves on to step 164, in which a test is made to determine whether or not the read pointer is greater than a maximum value. It is common to use on the order of a million good events in the calculation of an image, and thus the maximum number used in step 164 could be set to one million or any other desired number. Once the read pointer equals one million, the computer will have calculated one million points $X_0, Y_0$ and thus a good image should have been obtained. If the read pointer is less than the maximum number the program loops back to step 150 and continues to repeat itself until the read pointer reaches the maximum value. Once the read pointer does equal the maximum value, the program advances to step 166 in which the good event interrupt is disabled so that the computer will disregard any further interrupts generated by line 116, and then the program shown in FIG. 7 is exited.

If the pixel map which is added to in step 160 is shown directly on a videographic terminal as computer 44 performs the program of FIG. 7, it is possible for the operator of camera 10 to view the image of the radioactive source as it is being created and to turn off the operation of the program shown in FIG. 7 as soon as the image has a desired number of points calculated.

From the above description it should be clear that the gamma camera of the present invention discloses a solid state detecting means 34 for indicating the time, location, and energy of collisions between the detecting means and photons by sensing the occurrence, location and number of electron-hole pairs, respectively, generated by each such collision. The location of such collisions is indicated by the X and Y coordinates produced at the binary encoders $86_1$, $86_{2A}$, $86_{2B}$, $88_1$, $88_{2A}$, and $88_{2B}$ shown in FIG. 5. Similarly, the energy of such collisions is shown by the output of the output amplifiers $91_1$, $91_{2A}$, and $91_{2B}$ shown in FIG. 5. The time of such collisions is shown by the time of the signals $E_1$ and $E_2$ which are emitted respectively from the output amplifiers $91_1$, $91_{2A}$ and $91_{2B}$ of FIG. 5.

The apparatus of the present invention also includes selecting means for choosing as an ordered pair a selected pair of collisions which indicate a good event. This selecting means includes means, responsive to the time of collisions as indicated by the timing of signals $E_1$ and $E_2$, for identifying a pair of such collisions which occur at substantially the same time, indicating that the selected pair of collisions result from a common photon. These means include the AND gate 114 which causes a high signal to be produced at good event output 116 only if the output of comparators 106 and 110 indicate the occurrence of signals $E_1$ and $E_2$ which are virtually simultaneous, indicating that the collisions which have given rise to signals $E_1$ and $E_2$ resulted from an original photon which struck first detector 52 and caused the emission of a second photon which then collided with second detector 53. The means for selecting a good event further includes means responsive to the energies of the collisions indicated by the signals $E_1$ and $E_2$ for preventing a pair of collisions from being selected as a good event unless the energy associated with one of those collisions indicates the photoelectric absorption of a photon. This means includes comparator 110 which only produces a high signal at its output if the signal $E_2$ has an energy associated with photoelectric absorption. The selecting means further includes collision identifying means for selecting as the first collision of a good event that one of its two collisions which does not have associated with it energy indicating the photoelectric absorption of a photon. This collision identifying means includes the window detector 106 which produces a high output only if the signal $E_1$ has an energy between 5 keV and 50 keV, which is too low to result from photoelectric absorption. This selection of $E_1$ as the energy of the first collision is essential since, as is discussed above, the step 156 of the program shown in FIG. 7 calculates the angle of Compton scattering $\theta$ on the basis that $E_1$ is the energy associated with the Compton scattering and $E_2$ is the energy associated with the photoelectric absorption of a good event. The selecting means further includes means responsive to the energies of $E_1$ and $E_2$, for preventing a pair of collisions from being selected as a good event unless the sum of the energies $E_1$ and $E_2$ associated with that pair is within a predetermined range, i.e. the energy range expected from the particular source as discussed above. Summing amplifier 108 and window comparator 112 comprise this means, since they prevent AND gate 114 from having a high output unless the sum of $E_1$ and $E_2$ is within two percent of 140 keV for 99m-technetium as a source.

It can also be seen that the gamma camera shown above has a first line determining means responsive to output 116 of the good event selecting means and to the location of the collisions of a good event as indicated by the signals $X_1$, $Y_1$ and $X_2$, $Y_2$, $S_2$, for determining a collision line $L_1$ between the two collisions of a good event. This first line determining means includes not only the circuitry, such as latches 120, 122, 128, 130 and 132 which enable computer 44 to read the values of $X_1$, $Y_1$, $X_2$, $Y_2$, and $S_2$, but it also includes computer 44 and the programming contained at step 154 which enables the computer to calculate the collision line $L_1$. The gamma camera also includes angle determining means responsive to the energies $E_1$ and $E_2$ for determining the angle of scattering relative to the collision line $L_1$ which occurs at the first collision of a good event. This means includes not only pulse height analysis circuits 134 and 136 and latches 124 and 126 which enable computer 44 to read the values of $E_1$ and $E_2$, but it also includes computer 44 and the portion of the program contained at step 156 shown in FIG. 7 which enables the computer to calculate $\theta$ from the $E_1$ and $E_2$. The gamma camera further includes a second line determining means responsive to the location $X_1$, $Y_1$, the collision line $L_1$, and the angle $\theta$ for determining a second line $L_2$ parallel with the collimation plane 50 which forms the angle $\theta$ with the collision line $L_1$ at the location of the first collision, $X_1$, $Y_1$. This means includes those portions of computer 44 and the program shown in FIG. 7 used in calculation step 158.

Figure 8:
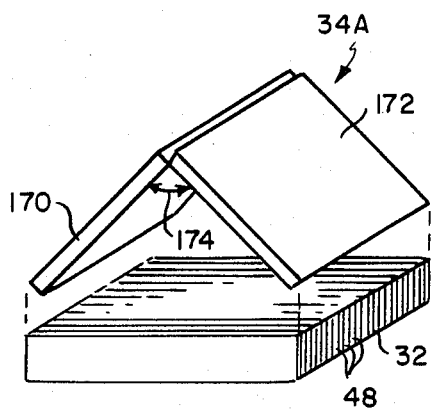
FIG. 8 is an exploded, perspective view of the solid-state detecting means and parallel plate collimator used in a second embodiment of the invention.
Figure 9:
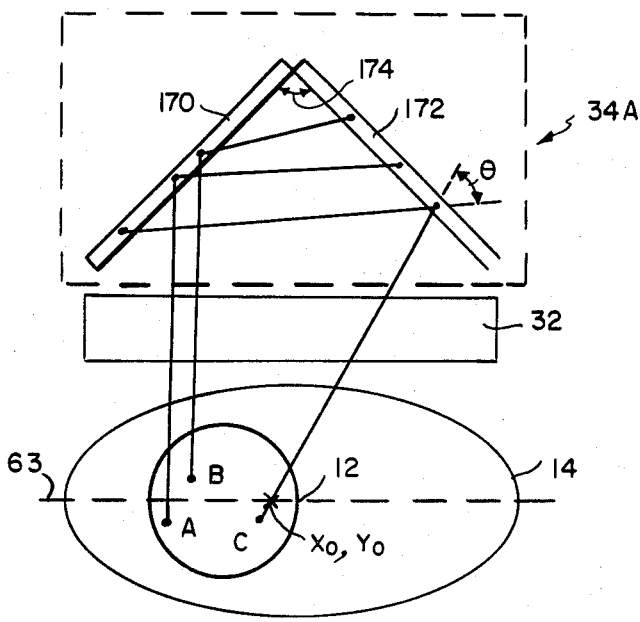
FIG. 9 is a simplified schematic view of the solid-state detecting means and parallel plate collimator of FIG. 8 illustrating a source of radiation and various photon paths emitted from that source.

Referring now to FIGS. 8–12, a second embodiment of a gamma camera according to the present invention is shown. In this embodiment parallel plate collimator 32 is identical to that shown in the previous embodiment. However, solid-state detecting means 34A of this embodiment is different from solid-state detecting means 34 shown in the previous embodiment in that it comprises semiconductor detectors 170 and 172 which are positioned relative to each other so that the planes of the plates of those two detectors intersect at an angle 174. In the preferred embodiment shown in FIGS. 8 and 9, angle 174 is ninety degrees, because this angle makes possible the catching of a relatively high number of the photons produced by Compton scattering in first collisions with either detectors 170 and 172 while at the same time not requiring an excessive amount of semiconductor to be used. However, in other embodiments the angle 174 could vary between about thirty and one hundred fifty degrees and still produce a functional, reasonably priced detecting means. The line formed by the intersection between the planes of the plate of detectors 170 and 172 is perpendicular to the planes of collimation plates 48 of collimator 32. The opening of angle 174 faces the position at which the source of photons 12 is to be placed during imaging so that a photon from the source 12 can have a collision with either of the two detectors 170 or 172, and then undergo a Compton scattering and have the resulting photon collide with the other of the two detectors. One of the advantages of the embodiment shown in FIGS. 8 and 9 is that the angles of Compton scattering which give rise to good events with it are larger, on the average, than those which give rise to good event in the previously shown embodiment. Such larger angles of Compton scattering result in greater energies of collision, which in turn enable more accurate calculation of such scattering angles.

The detectors 170 and 172 are made of germanium and are formed of a composite of crystals in a manner similar to that illustrated in FIG. 4. The size of the detecting means 34A is sufficiently large so that the roof shaped structure formed by the two detectors 170 and 172 covers an area of approximately thirty centimeters by thirty centimeters, and each of the detectors 170 and 172 is approximately one centimeter thick. Since the detectors of the solid-state detecting means 34A are made of germanium, it is desirable to cool them in a low temperature, preferably cryogenic, environment in order to prevent an undesirably high level of thermal noise. Cooling these detectors with liquid nitrogen at 77° Kelvin will provide quite adequate cooling for such a purpose.

Figure 10:
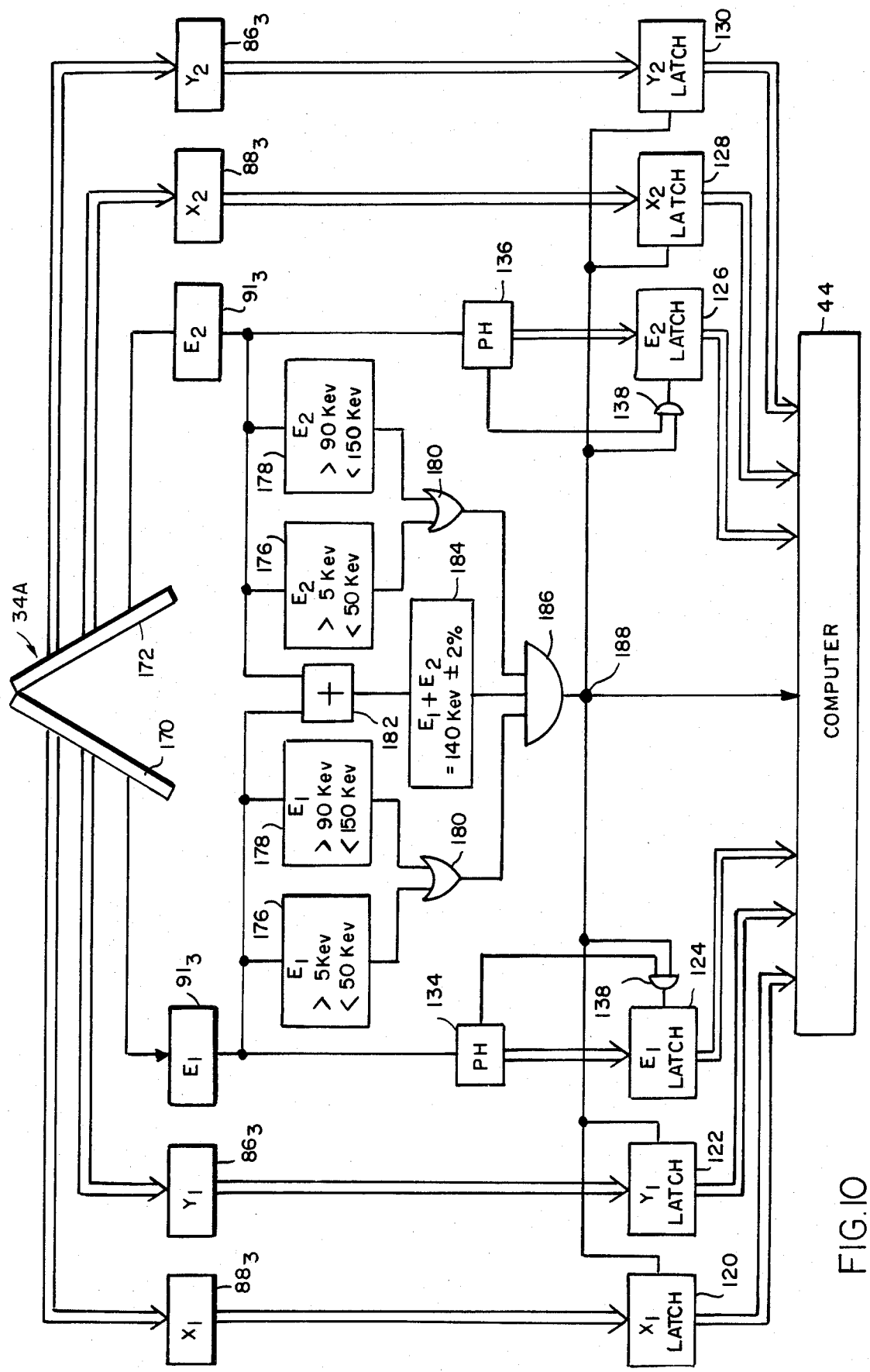
FIG. 10 is a schematic representation of electronic circuitry used in conjunction with the embodiment of the invention shown in FIGS. 8-9.

FIG. 10 shows the electronics which are used in a gamma camera having a solid-state detector 34A, such as is shown in FIGS. 8 and 9. As can be seen from FIG. 10 the circuit elements associated with the first and second detectors 170 and 172 are identical, and are numbered identically. The $X_1$, $Y_1$, and $E_1$ outputs from the first detector 170 are provided at binary encoders $88_3$ and $86_3$, and at output amplifier $91_3$, respectively, which correspond to the binary encoders 88, $88_1$, $88_{2A}$ and $88_{2B}$ and 86, $86_1$, $86_{2A}$ and $86_{2B}$, and to output amplifier 91, $91_1$, $91_{2A}$ and $91_{2B}$, respectively, shown in FIGS. 4 and 5. Similarly, the $X_2$, $Y_2$ and $E_2$ outputs of the second detector 172 are supplied to similarly numbered binary encoders $88_3$, $86_3$, and $91_3$. The analog output of each of the output amplifiers $91_3$ is supplied to the inputs of a first window comparator 176 and a second window comparator 178. Each window comparator 176 produces a binary output which is high only when the signal supplied to it has an energy greater than 5 keV and less than 50 keV. This energy range is associated with Compton scattering at an angle which is sufficiently great to enable accurate calculation of the angle of such scattering. Each window comparator 178 produces a binary output which is high only when the signal supplied to it indicates an energy of collision between 90 keV and 150 keV, which indicates the occurrence of a photoelectric absorption. The output of each of the window comparators 176 and 178 which is supplied from a given output amplifier $91_3$ is supplied to the input of an OR gate 180 which produces a high output only when at least one of its two inputs is high. Thus the output of an OR circuit 180 will have a high signal only if the signal $E_1$ or $E_2$ supplied from its associated output amplifier $91_3$ indicates either a Compton scattering or a photoelectric absorption.

The output of each of the amplifiers $91_3$ is also supplied to the input of a common summing amplifier 182. The summed signal $E_1+E_2$ produced at the output of amplifier 182 is provided as an input to a window comparator 184 which produces a binary output which is high only if the sum of $E_1$ and $E_2$ is equal to 140 keV plus or minus two percent. Thus when the output of the window comparator 184 is high the circuitry of FIG. 10 indicates that a pair of collisions have taken place in detectors 170 and 172 which have a total energy very close to the energy of a photon emitted directly by 99m-technetium. It should be noted that the energies associated with the window comparators 176, 178, and 184 can be changed when the gamma camera shown in FIG. 10 is being used with radioactive isotopes which emit photons having an energy other than 140 keV.

The output of the two OR gates 180 and the window comparator 184 are each supplied to the inputs of an AND gate 186. The good event output 188 of AND gate 186 is high only if all three of the inputs to AND gate 186 are high at the same time. When this occurs a good event is indicated, because for all three inputs to AND gate 186 to be high at the same time it is necessary for two collisions to have occurred, one in each of the detectors 170 and 172, at substantially the same time, and for the sum of those two collisions to have an energy approximately equal to 140 keV, the energy associated with a photon emitted directly by 99m-technetium. In order for the sum of $E_1$ and $E_2$ to equal approximately 140 keV when the two outputs from the OR gates 180 are both high, one of the detectors 170 or 172 will necessarily have detected a collision with an energy between 5 and 20 keV, indicating Compton scattering, and the other of the two detectors will necessarily have detected a collision with an energy between 90 and 150 keV, indicating photoelectric absorption.

When a high signal is generated at the good event output 188, the X, Y, and E outputs of each of detectors 170 and 172 are stored in latches 120–130, which function in the same manner as the similarly numbered latches in FIG. 5. The analog outputs of the amplifiers $91_3$ pass through pulse height analysis circuits 134 or 136. The operation of pulse height analysis circuits 134 and 136, latches 124 and 126, and the AND gates 138 in FIG. 10 is the same as that of similarly numbered elements in FIG. 5. The good event output 188 is also supplied as an interrupt to a computer 44 so that when a high signal is generated on that line, computer 44 will perform the interrupt subroutine illustrated in FIG. 11, causing that computer to read the values stored in the latches 120–130.

Figure 11:
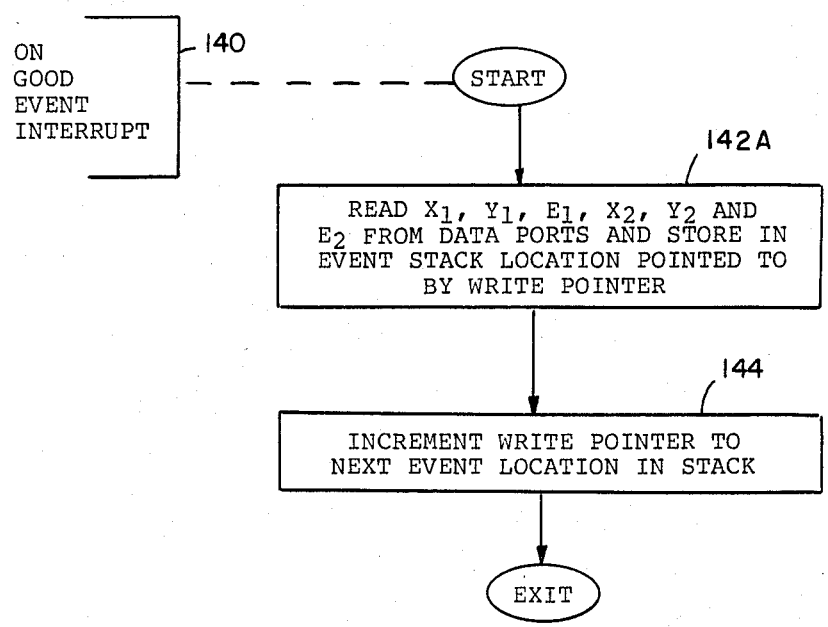
FIGS. 11-12 are block diagrams illustrating an embodiment of the computational steps used to create an image of a photon source for the camera of FIGS. 8-10.

Referring now to FIG. 11, the interrupt subroutine which computer 44 undergoes in the embodiment of the invention shown in FIGS. 8-10 is identical to that shown in FIG. 6, except that in its step 142A shown in FIG. 11 there is no value $S_2$ to be read from a data port, since none of the detectors of the embodiment shown in FIGS. 8-10 has more than one side, and thus there is no need for data corresponding to $S_2$ to be generated or read.

Figure 12:
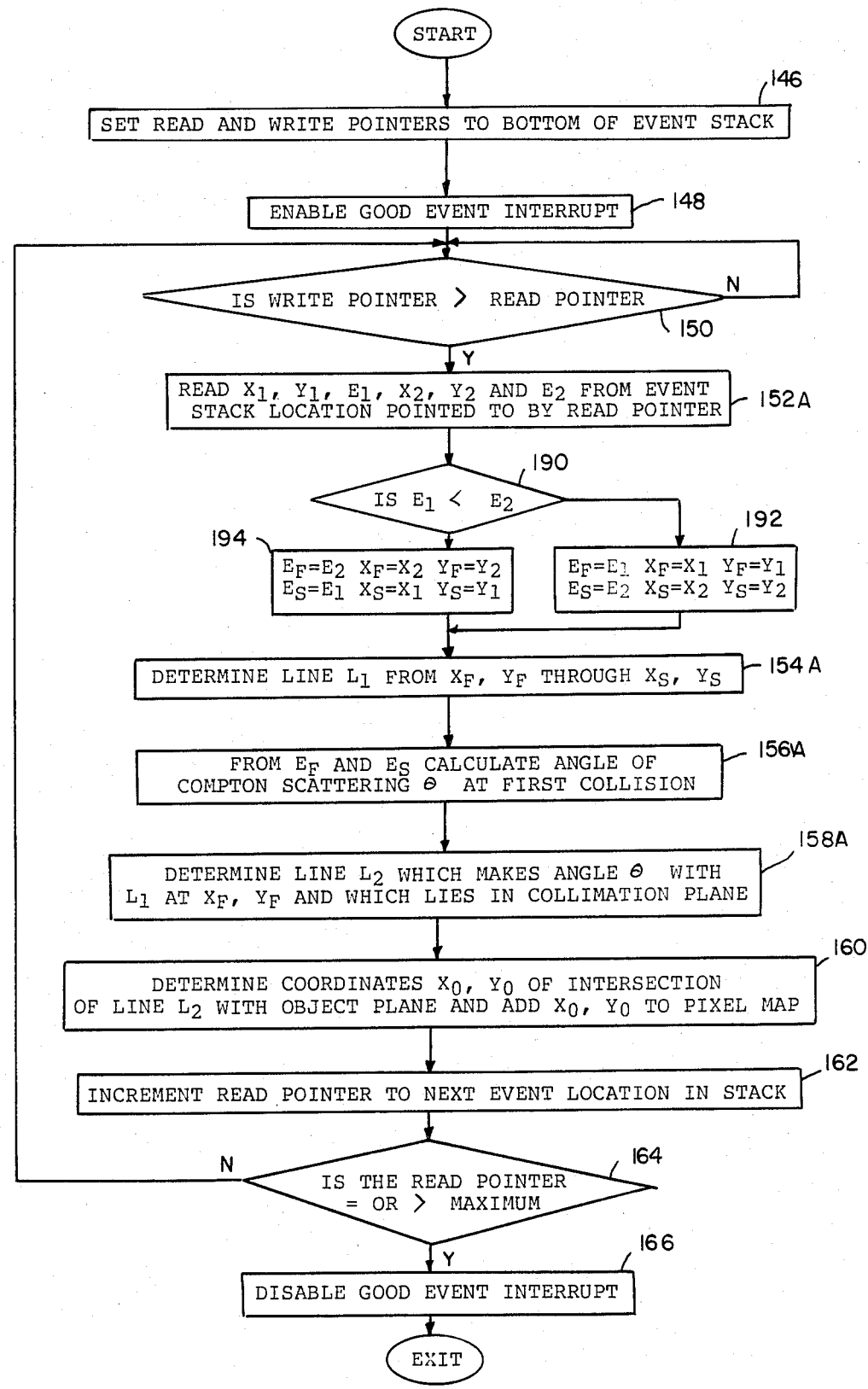

Referring now to FIG. 12, a flow chart of the program computer 44 uses in the embodiment of the invention shown in FIGS. 8-10 to calculate points $X_0$, $Y_0$ of a radiological image is illustrated. This program is similar to that shown in FIG. 7, and its steps which are identical to those shown in FIG. 7 are labeled with identical numbers. The first difference between the programs of FIGS. 7 and 12 is that the values read from the event stack location pointed to by the read pointer in steps 152A of FIG. 12 do not include a value $S_2$, because, as has been stated above, there is no use for such a value in the embodiment of the invention shown in FIGS. 8-10.

Another difference between the programs of FIGS. 7 and 12 results from the fact that the embodiment of the invention shown in FIGS. 8-10 does not always have the first collision of a good event associated with the same detector, as does the embodiment of the invention shown in FIGS. 1, 2, 3, and 5. Therefore it is necessary for steps 190, 192, and 194 to be added to the program in FIG. 12 so that it can determine which of the values $X_1$, $Y_1$, and $E_1$ or $X_2$, $Y_2$, and $E_2$ stored in its event stack are associated with the first collision at which Compton scattering has taken place and which are associated with the second collision at which photoelectric absorption has taken place. In step 190 a test is made to see whether $E_1$ is less than $E_2$. If it is, the program advances to step 192 in which a variable $E_F$, representing the energy of the first collision, is set equal to $E_1$, a variable $X_F$, representing the X coordinate of the first collision, is set to $X_1$, and a variable $Y_F$, representing the Y coordinate of the first collision, is set equal to $Y_1$. Similarly variables $E_S$, $X_S$, and $Y_S$, associated with the second collision, are set equal to $E_2$, $X_2$, and $Y_2$, respectively. If $E_1$ is not less than $E_2$, then it is clear, because of the operation of window comparators 176, 178, and 184, that $E_1$ has the greater energy, and thus the collision associated with it must have been the second collision of the good event, the one in which photoelectric absorption took place. In this case the program advances to step 194 in which variables $E_F$, $X_F$, and $Y_F$ associated with the first collision are set equal to $E_2$, $X_2$, and $Y_2$, respectively, and variables $E_S$, $X_S$, and $Y_S$ associated with the second collision are set equal to $E_1$, $X_1$, and $Y_1$ respectively.

Once the program has determined which values are to be associated with the first and second collisions, respectively, it advances to steps 154A, 156A and 158A which are identical to the steps 154, 156, and 158 shown in FIG. 7, except for the fact that variables $E_F$, $X_F$, $Y_F$, $E_S$, $X_S$ and $Y_S$ are used instead of $E_1$, $X_1$, $Y_1$, $E_2$, $X_2$, $Y_2$ and $S_2$ as in the corresponding steps of FIG. 7.

All of the remaining steps of the program shown in FIG. 12 are identical to those shown in FIG. 7.

Thus it can be seen that the second embodiment of the invention described with reference to FIGS. 8-12 enables the path of a photon which results in a good event, to be determined, and the intersection of that path with an object plane 63 to be calculated so as to give rise to a point $X_0$, $Y_0$, which can be used to create an image of the radiation source from which such a photon came.

From the above description including preferred embodiments it can be seen that the present invention makes it possible to construct a gamma camera which has a higher resolution than that which is found with many gamma cameras of the prior art, which has a very high ability to discriminate against photons which have resulted from unwanted Compton scattering, greatly increasing the clarity of the image which is produced, and which has a higher count rate per minute per microcurie of radioactive source material used, enabling gamma cameras according to the present invention to create images either at a greater speed or at a lower dosage of radioactive source material than most gamma cameras in the prior art.

It should be understood that many varied embodiments of the present invention are possible. For example, it is possible to create a gamma camera which calculates the angle of Compton scattering at the site of the first of two collisions of a good event in the same manner as the embodiments of the invention described above, but which does not have the parallel plate collimator used in those embodiments. Because it lacks a parallel plate collimator, such a gamma camera would generally require tomographic techniques to determine an image of a radioactive source, and thus it would not be as fast as the preferred embodiments of the invention described above. Nevertheless it would have a high ability to reject photons emitted by unwanted Compton scattering. Similarly, it is possible to make a gamma camera according to the present invention in which the solid-state detector used has a configuration different than that set forth in the embodiments which have been described herein. Furthermore, it should be obvious to those skilled in the computer programming arts, that many programs other than those disclosed above could be used to cause this invention to function as recited in the claims below.

Thus, there has been described a new and improved gamma camera, having significant advantages over the previous devices used in the prior art for producing images of radioactive sources. It should be appreciated that modifications to the described embodiments may be made by those of ordinary skill applying the principles of the present invention. Accordingly, the present invention should not be considered to be limited by the description herein of the preferred embodiments, but rather should be interpreted in accordance with the following claims.

What is claimed is:

1. A gamma camera for creating the image of the radiation density of a source of photons located in a predetermined position relative to said camera, said camera comprising:

detecting means comprising a solid-state material capable of generating electron-hole pairs as a result of collisions between photons and said material and means for determining the time, location and energy dissipated in such a collision by sensing the occurrence, the location, and the number of electron-hole pairs, respectively, generated by said collision, said detecting means being capable of so determining the time, location and energy of each of two such collisions which result from a common photon;

identifying means for identifying an ordered pair of said collisions in which both collisions result from a common photon;

means for determining an image of said source of said common photon from the locations of, and the number of electron-hole pairs generated by said ordered pair of collisions.

2. A gamma camera according to claim 1 in which said identifying means further includes means, responsive to the energies of said collisions indicated by said detecting means, for preventing a pair of said collisions from being identified as said ordered pair unless the energy associated with one of those collisions indicates the photoelectric absorption of a photon.

3. A gamma camera according to claim 2 in which said identifying means further includes means, responsive to the energies of said collisions indicated by said detecting means, for preventing a pair of said collisions from being identified as said ordered pair unless the sum of the energies associated with that pair of collisions is within a predetermined range.

4. A gamma camera according to claim 1 in which said detecting means includes at least two detectors, each made of semiconducting material, and each capable of determining the time, location, and energy of collisions between its semiconducting material and photons by sensing the occurrence, location and number of electron-hole pairs, respectively, generated by each such collision, said detectors being oriented relative to each other so that a photon produced in a collision detected in a first of said detectors can produce a collision which is detected in the other of said detectors.

5. A gamma camera according to claim 4 in which two of said detectors includes a generally plate-shaped portion of semiconducting material, one surface of each said plate-shaped portion having attached thereto at least one electrode for determining the position of said collisions along a first direction in the plane of said surface and the other, opposite, surface of each said plate-shaped portion having attached thereto at least one electrode for determining the position of said collisions along a second direction in the plane of said other surface.

6. A gamma camera according to claim 5 in which two of said detectors are positioned relative to each other and said source position so that the planes of said plate-shaped portions of said two detectors intersect in an angle which faces said source position, and so that a photon from said source can have a collision with either of said two detectors, undergo Compton scattering and have the resulting photon collide with the other of said two detectors.

7. A gamma camera according to claim 5 in which said two detectors are oriented at generally right angles relative to each other.

8. A gamma camera according to claim 5 in which said first and second detectors are positioned relative to said source position so that photons emitted directly from said source are more likely to hit said first detector than said second detector and said detectors are positioned relative to each other so that photons resulting from Compton scattering in said first detector can collide with said second detector.

9. A gamma camera according to claim 8 in which a planar dimension of said first detector is positioned generally perpendicularly to the shortest line between said first detector and said source position, and said second detector is positioned generally perpendicularly to said planar dimension of said first detector.

10. The gamma camera according to claim 1 in which said image determining means further includes:

first line determining means, responsive to said identifying means and to the locations of said collisions of said ordered pair determined by said detecting means, for determining a collision line between said collisions of said ordered pair;

angle determining means, responsive to the energy of each of said collisions of said ordered pair as determined by said detecting means, for determining the angle of Compton scattering relative to said collision line which occurs at a first of said collisions of said ordered pair, and parallel plate collimator means placed between said detecting means and said source position for determining a second line parallel with said collimator means which forms said Compton scattering angle with said collision line at said location of said first collision.

11. A gamma camera according to claim 10 further including means for selecting as said first collision, at which said angle of Compton scattering is determined by said angle determining means, that one of said ordered pair's two collisions which does not have associated with it energy dissipated in an amount indicating the photoelectric absorbtion of a photon.

12. A gamma camera for creating an image of the radiation density of a source of photons located in a predetermined source position relative to said camera, said gamma camera comprising:

solid-state detecting means for determining the time, location, and energy of collisions between said detecting means and photons by sensing the occurrence, location and number of electron-hole pairs, respectively, generated by each such collision, said detecting means being capable of so determining the time, location and energy of each of two collisions which result from a common photon;

a parallel plate collimator placed between said detecting means and said source position so that the substantial majority of photons which reach said detecting means from said source of photons are traveling generally parallel to a known collimation plane;

selecting means for choosing as an ordered pair a selected pair of said collisions, said selecting means including means, responsive to the time of said collisions indicated by said detecting means, for selecting a pair of said collisions which occur at substantially the same time, indicating that said ordered pair of collisions results from a common photon;

first line determining means, responsive to said selecting means and to the locations of said collisions of said ordered pair indicated by said detecting means, for determining a collision line between said collisions of said ordered pair;

angle determining means responsive to the energy of a predetermined one of said collisions of said ordered pair as determined by said detecting means and said selecting means for determining the angle of Compton scattering relative to said collision line which occurs at a first of said collisions of said ordered pair; and second line determining means, responsive to the location of said first collision of said ordered pair indicated by said detecting means, said collision line determined by said first line determining means, and said Compton scattering angle determined by said angle determining means, for determining a second line parallel with said collimation plane which forms said Compton scattering angle with said collision line at said location of said first collision.

13. A gamma camera according to claim 12 in which said selecting means further includes means, responsive to the energies of said collisions indicated by said detecting means, for preventing a pair of said collisions from being selected as said ordered pair unless the energy associated with one of those collisions indicates the photoelectric absorption of a photon.

14. A gamma camera according to claim 13 in which said selecting means further includes means, responsive to the energies of said collisions indicated by said detecting means, for preventing a pair of said collisions from being selected as said ordered pair unless the sum of the energies associated with that pair of collisions is within a predetermined range.

15. A gamma camera according to claim 13 further including means for selecting as said first collision, at which said angle of Compton scattering is determined by said angle determining means, that one of said ordered pair's two collisions which does not have associated with it energy dissipated in an amount indicating the photoelectric absorption of a photon.

16. A gamma camera according to claim 12 in which said angle determining means is responsive to the energy of each of said collisions of said ordered pair as indicated by said detecting means in its determination of said angle of Compton scattering.

17. A gamma camera according to claim 12 in which said detecting means includes at least two detectors, each made of semiconducting material, and each capable of determining the time, location, and energy of collisions between its semiconducting material and photons by sensing the occurrence, location and number of electron-hole pairs, respectively, generated by each such collision, said detectors being oriented relative to each other so that a photon produced in a collision detected in a first of said detectors can produce a collision which is detected in the other of said detectors.

18. A gamma camera according to claim 17 in which each of said detectors includes a generally plate-shaped portion of semiconducting material, one surface of each said plate-shaped portion having attached thereto at least one electrode for determining the position of said collisions along a first direction in the plane of said surface and the other, opposite, surface of each said plate-shaped portion having attached thereto at least one electrode for determining the position of said collisions along a second direction in the plane of said other surface.

19. A gamma camera according to claim 18 in which two of said detectors are positioned relative to each other and said source position so that the planes of said plate shaped portions of said two detectors intersect in an angle which faces said source position, and so that a photon from said source can have a collision with either of said two detectors, undergo Compton scattering and have the resulting photon collide with the other of said two detectors.

20. A gamma camera according to claim 19 in which said collimation plane of said parallel plate collimator is perpendicular to the intersection of the planes of said plate shaped portions of each of said two detectors.

21. A gamma camera according to claim 18 in which said two detectors are oriented at generally right angles relative to each other.

22. A gamma camera according to claim 18 in which said first and second detectors are positioned relative to said source position so that photons emitted directly from said source are more likely to hit said first detector than said second detector and said detectors are positioned relative to each other so that photons resulting from Compton scattering in said first detector can collide with said second detector.

23. A gamma camera according to claim 22 in which a planar dimension of said first detector is positioned generally perpendicularly to the shortest line between said first detector and said source position, and said second detector is positioned generally perpendicularly to said plate-shaped portion of said first detector.

24. A gamma camera for creating an image of the radiation density of a source of photons located in a predetermined source position relative to said camera, said gamma camera comprising:

solid-state detecting means for determining the time, location, and energy of collisions between said detecting means and photons by sensing the occurrence, location and number of electron-hole pairs, respectively, generated by each such collision, said detecting means being capable of so determining the time, location and energy of each of two collisions which result from a common photon;

a parallel plate collimator placed between said detecting means and said source position so that the substantial majority of photons which reach said detecting means from said source of photons are traveling generally parallel to a known collimation plane;

selecting means for choosing as an ordered pair a selected pair of said collisions, said selecting means including means, responsive to the time of said collisions indicated by said detecting means, for selecting a pair of said collisions which occur at substantially the same time, indicating that said ordered pair of collisions results from a common photon;

first line determining means, responsive to said selecting means and to the locations of said collisions of said ordered pair determined by said detecting means, for determining a collision line between said collisions of said selected pair;

angle determining means, responsive to the energy of a predetermined one of said collisions of said ordered pair as determined by said detecting means and said selecting means, for determining the angle of Compton scattering relative to said collision line which occurs at a first of said collisions of said ordered pair; and second line determining means, responsive to the location of said first collision of said ordered pair indicated by said detecting means, said collision line determined by said first line determining means, and said Compton scattering angle determined by said angle determining means, for determining a second line parallel with said collimation plane which forms said Compton scattering angle with said collision line at said location of said first collision;

said detecting means including first and second separate detectors, each detector comprising semiconducting material, said first detector comprising a semiconducting material having a lower average atomic weight than said second detector, and said first and second detectors being positioned relative to said source position so that photons emitted directly from said source are more likely to hit said first detector than said second detector and said detectors being positioned relative to each other so that photons resulting from Compton scattering in said first detector can collide with said second detector.

25. A gamma camera according to claim 24 in which a majority of the atoms of said semiconducting material of said first detector are of silicon and a majority of the atoms of said semiconducting material of said second detector are of germanium.

26. A gamma camera according to claim 24 in which said first and second detectors each include a generally plate shaped portion comprised of semiconducting material, one surface of each said plate-shaped portion having attached thereto at least one electrode for determining the position of said collisions along a first direction in the plane of said surface and the other, opposite, surface of each said plate-shaped portion having attached thereto at least one electrode for determining the position of said collisions along a second direction in the plane of said other surface.

27. A gamma camera according to claim 26 in which said plate-shaped portion of said first detector is at least one and a half times thicker than said plate shaped portion of said second detector.

28. A gamma camera according to claim 26 in which said first detector includes one of said plate shaped portions positioned generally perpendicular to a line between said plate-shaped portion of said first detector and said source position and said second detector includes at least one of said plate-shaped portions positioned generally perpendicular to said plate-shaped portion of said first detector.

29. A gamma camera according to claim 28 in which said plate shaped portion of said first detector includes a target portion in which a substantial majority of collisions between photons from said source and said first detector take place and in which said at least one plate-shaped portion of said second detector is positioned perpendicular to said plate shaped portion of said first detector at a location outside said target portion.

30. A gamma camera according to claim 29 in which said at least one plate-shaped portion of said second detector is located generally on the opposite side of said plate-shaped portion of said first detector from said source position.

31. A gamma camera according to claim 29 in which said second detector includes four of said plate-shaped portions, one located perpendicular to said plate shaped portion of said first detector along each of four sides of a rectangle which surrounds said target portion of said first detector.

32. A gamma camera for creating an image of the radiation density of a source of photons located in a predetermined source position relative to said camera, said gamma camera comprising:
    solid-state detecting means including at least two detectors, each made of semiconducting material, and each for determining the time, location, and energy of collisions, between it and photons by sensing the occurrence, location and number of electron-hole pairs, respectively, generated by each such collision, said detectors being oriented relative to each other so that a photon produced in a collision detected in a first of said detectors can produce a collision which is detected in the other of said detectors;
    a parallel plate collimator placed between said detecting means and said source position so that the substantial majority of photons which reach said detecting means from said source of photons are traveling generally parallel to a known collimation plane;
    selecting means for choosing as an ordered pair a selected pair of said collisions, said selecting means including means, responsive to the time of said collisions indicated by said detecting means, for selecting a pair of said collisions which occur at substantially the same time, indicating that said ordered pair of collisions results from a common photon, means responsive to the energies of said collisions indicated by said detecting means, for preventing a pair of said collisions from being selected as said ordered pair unless the energy associate with one of those collisions indicates the photoelectric absorption of a photon, and means, responsive to the energies of said collisions indicated by said detecting means, for preventing a pair of said collisions from being selected as said ordered pair unless the sum of the energies associated with that pair of collisions is within a predetermined range;
    means for selecting as the first collision of said ordered pair that one of said ordered pair's two collisions which does not have associated with it energy dissipated in an amount indicating the photoelectric absorption of a photon;
    first line determining means, responsive to said selecting means and to the locations of said collisions of said ordered pair indicated by said detecting means, for determining a collision line between said collisions of said ordered pair;
    angle determining means, responsive to the energy of a predetermined least one of said collisions of said ordered pair as indicated by said detecting means and said selecting means, fo determining the angle of Compton scattering relative to said collision line which occurs at said first collision; and
    second line determining means, responsive to the location of said first collision of said ordered pair indicated by said detecting means, said collision line determined by said first line determining means, and said Compton scattering angle determined by said angle determining means, for determining a second line parallel with said collimation plane which forms said Compton scattering angle with said collision line at said location of said first collision.

33. A gamma camera according to claim 32 in which said angle determining means is responsive to the energy of each of said collisions of said ordered pair as indicated by said detecting means in its determination of said angle of Compton scattering.

34. A gamma camera according to claim 32 in which each of said detectors includes a generally plate-shaped portion of semiconducting material, one surface of each said plate shaped portion having attached thereto at least one electrode for determining the position of said collisions along a first direction in the plane of said surface and the other, opposite, surface of each said plate-shaped portion having attached thereto at least one electrode for determining the position of said collisions along a second direction in the plane of said other surface.

35. A gamma camera for creating an image of the radiation density of a source of photons located in a predetermined source position relative to said camera, said gamma camera comprising:

solid-state detecting means including a first and a second separate detector, each comprising semiconducting material, and each for determining the time, location, and energy of collisions between it and photons by sensing the occurrence, location and number of electron-hole pairs, respectively, generated by each such collision, said first detector comprising a semiconducting material having a lower average atomic weight than said second detector, and said first and second detectors being positioned relative to said source position so that photons emitted directly from said source are more likely to hit said first detector than said second detector and said detectors being positioned relative to each other so that photons resulting from a Compton scattering detected in said first detector can collide with and be detected by said second detector;

a parallel plate collimator placed between said detecting means and said source position so that the substantial majority of photons which reach said detecting means from said said source of photons are traveling generally parallel to a known collimation plane;

selecting means for choosing as an ordered pair a selected pair of said collisions, said selecting means including means, responsive to the time of said collisions indicated by said detecting means, for selecting a pair of said collisions which occur at substantially the same time, indicating that said ordered pair of collisions results from a common photon, means responsive to the energies of said collisions indicated by said detecting means, for preventing a pair of said collisions from being selected as said ordered pair unless the energy associated with one of those collisions indicates the photoelectric absorption of a photon, and means, responsive to the energies of said collisions indicated by said detecting means, for preventing a pair of said collisions from being selected as said ordered pair unless the sum of the energies associated with that pair of collisions is within a predetermined range;

means for selecting as the first collision of said ordered pair that one of said ordered pair's two collisions which does not have associated with it energy dissipated in an amount indicating the photoelectric absorbtion of a photon;

first line determining means, responsive to said selecting means and to the locations of said collisions of said ordered pair indicated by said detecting means, for determining a collision line between said collisions of said ordered pair;

angle determining means, responsive to the energy of a predetermined one of said collisions of said ordered pair as indicated by said detecting means and said selecting means, for determining the angle of Compton scattering relative to said collision line which occurs at said first collision; and second line determining means, responsive to the location of said first collision of said ordered pair indicated by said detecting means, said collision line determined by said first line determining means, and said Compton scattering angle determined by said angle determining means, for determining a second line parallel with said collimation plane which forms said Compton scattering angle with said collision line at said location of said first collision.

36. A gamma camera according to claim 35 in which a majority of the atoms of said semiconducting material of said first detector are of silicon and a majority of the atoms of said semiconducting material of said second detector are of germanium.

37. A gamma camera according to claim 35 in which said first detector is significantly thicker in the direction in which photons emitted directly from said source position pass into said first detector than said second detector is in the direction in which most of the photons emitted by Compton scattering in said first detector pass into said second detector.

38. A method of creating an image of the radiation density of a source of photons located on a predetermined position, said method comprising the steps of:

detecting the time, location and energy dissipated in collisions between photons and solid-state material capable of generating electron-hole pairs as a result of such collisions, including determining the energy dissipated in said detected collisions by sensing the number of electron-hole pairs generated by said collisions;

identifying an ordered pair of said collisions so detected in which both collisions result from a common photon; and determining an image of said source of said common photon from the location of, and the number of electron-hole pairs generated by said ordered pair of collisions.

39. A method according to claim 38 in which said step of detecting further includes determining said time and location of said collisions by sensing the occurrence and location of said electron-hole pairs generated by said collisions.

40. A method according to claim 38 in which said step of identifying further includes preventing a pair of said collisions from being identified as said ordered pair unless the energy associated with one of those collisions, as said energy is determined by said sensing of electron-hole pairs, indicates the photoelectric absorption of a photon, and unless the sum of the energies associated with that pair of collisions, as said energies are determined by said sensing of electron-hole pairs, is within a predetermined range.

41. A method of creating an image of the radiation density of a source of photons located in a predetermined position, said method comprising the steps of:

causing photons from said source to pass through a parallel plate collimator so that they travel generally parallel to a collimation plane;

determining the time, location and energy of collisions between photons which have passed through said collimator and a solid-state material by sensing the occurrence, location and number of electron-hole pairs generated by each such collision;

choosing as an ordered pair a selected pair of said collisions which occur at substantially the same time, as determined by said sensing of electron-hole pairs, indicating that said ordered pair of collisions result from a common photon;

determining a collision line between the locations of said collisions of said ordered pair, as said locations are determined by said sensing of electron-hole pairs;

determining the angle of Compton scattering relative to said collision line which occurs at a first of said collisions of said ordered pair in response to the energy of a predetermined one of said collisions of said ordered pair, as said energy is determined by said sensing of electron-hole pairs; and determining a second line parallel with the collimation plane which forms said Compton scattering angle with said collision line at the location of said first collision, as said location is determined by said sensing of electron-hole pairs.

42. A method of creating an image of the readiation density of a source of photons located in a predetermined position, said method comprising the steps of:

causing photons from said source to pass through a parallel plate collimator so that they travel generally parallel to a collimation plane;

determining the time, location and energy of collisions between photons and a solid-state material by sensing the occurrence, location and number of electron-hole pairs generated by each such collision;

choosing as an ordered pair a selected pair of said collisions which occur at substantially the same time, as determined by said sensing of electron-hole pairs, indicating that said ordered pair of collisions result from a common photon, and preventing a pair of said collisions from being selected as said ordered pair unless the energy associated with one of those collisions, as said energy is determined by said sensing of electron-hole pairs, indicates the photoelectric absorption of a photon and unless the sum of the energies associated with that pair of collisions, as said energies are determined by said sensing of electron-hole pairs, is within a predetermined range;

determining a collision line between the locations of said collisions of said ordered pair, as said locations are determined by said sensing of electron-hole pairs;

determining the angle of Compton scattering relative to said collision line which occurs at a first of said collisions of said ordered pair in response to the energy of a predetermined one of said collisions of said ordered pair, as said energy is determined by said sensing of electron-hole pairs; and determining a second line parallel with the collimation plane which forms said Compton scattering angle with said collision line at the location of said first collision, as said location is determined by said sensing of electron-hole pairs.

* * * * *